(12) United States Patent
Castellano et al.

(10) Patent No.: US 6,500,239 B2
(45) Date of Patent: Dec. 31, 2002

(54) SYSTEM AND METHOD FOR REMOVING DISSOLVED GAS FROM A SOLUTION

(75) Inventors: Thomas P. Castellano, Los Angeles, CA (US); Eloy A. Ituarte, Reno, NV (US)

(73) Assignee: Penjet Corporation, Los Angeles, CA (US)

( * ) Notice: Subject to any disclaimer, the term of this patent is extended or adjusted under 35 U.S.C. 154(b) by 48 days.

(21) Appl. No.: 09/808,511

(22) Filed: Mar. 14, 2001

(65) Prior Publication Data

US 2002/0129705 A1 Sep. 19, 2002

(51) Int. Cl.$^7$ ............................................... B01D 19/00
(52) U.S. Cl. ............................ 95/247; 95/248; 95/250; 95/266; 141/18; 141/69; 206/528; 210/188; 222/190; 604/68; 604/187
(58) Field of Search ..................... 210/188; 604/406, 604/408, 68, 187; 206/528, 365; 222/152, 1, 190; 141/18, 69; 95/241, 245, 246, 247, 248, 250, 251, 252, 254, 260, 263, 266, 30; 96/155, 193, 202, 218, 175, 216, 204, 195, 196

(56) References Cited

U.S. PATENT DOCUMENTS

| | | | |
|---|---|---|---|
| 1,997,129 A | | 4/1935 | Taylor et al. |
| 2,221,739 A | | 11/1940 | Reiter |
| 2,500,916 A | * | 3/1950 | Whaley, Jr. |
| 2,605,763 A | | 8/1952 | Smoot |
| 2,632,445 A | | 3/1953 | Kas, Sr. |
| 2,642,062 A | | 6/1953 | May |
| 2,695,023 A | | 11/1954 | Brown |
| 2,718,299 A | | 9/1955 | Atwater et al. |
| 3,110,310 A | | 11/1963 | Cislak |
| 3,141,583 A | | 7/1964 | Mapel et al. |
| 3,293,749 A | | 12/1966 | George et al. |

(List continued on next page.)

FOREIGN PATENT DOCUMENTS

| | | |
|---|---|---|
| CA | 1103314 | 2/1978 |
| CA | 1 258 019 | 8/1989 |
| CH | 293302 | 9/1953 |
| DE | 730971 | 12/1942 |
| DE | 1 070 784 | 12/1959 |
| DE | 22140 | 10/1961 |
| EP | 0 037 696 A1 | 3/1981 |
| EP | 0 143 895 A1 | 8/1984 |
| EP | 0 220 146 A1 | 10/1986 |
| EP | 0 295 917 A1 | 6/1988 |

(List continued on next page.)

Primary Examiner—Duane S. Smith
(74) Attorney, Agent, or Firm—Pillsbury Winthrop LLP

(57) ABSTRACT

A system and multiple methods are described for removing dissolved gases from a liquid either prior to or following filling into a container. Prior to filling, gas is removed by creating a pressure differential, by application of heat, by sonication, or by generating a liquid by combination of dry solute and de-gassed solvent. Alternatively, liquids may be highly concentrated with solute to force any dissolved gas out of solution and later diluted with de-gassed solvents. In other embodiments, gases are percolated into liquids to displace atmospheric gases, wherein these percolated gases separate from solution and diffuse out of sealed contained after filling either by nature of their molecular size or chemical reaction with materials constructed into the container.

55 Claims, 12 Drawing Sheets

U.S. PATENT DOCUMENTS

| | | |
|---|---|---|
| 3,348,545 A | 10/1967 | Sarnoff et al. |
| 3,481,510 A | 12/1969 | Allen |
| 3,507,276 A | 4/1970 | Burgess |
| 3,517,668 A | 6/1970 | Brickson |
| 3,583,399 A | 6/1971 | Ritsky |
| 3,602,395 A * | 8/1971 | Krech |
| 3,608,272 A | 9/1971 | Di Peri et al. |
| 3,676,983 A | 7/1972 | Nold |
| 3,688,765 A | 9/1972 | Gasaway |
| 3,695,266 A | 10/1972 | Lussier |
| 3,793,805 A | 2/1974 | Hoffman |
| 3,853,125 A | 12/1974 | Clark et al. |
| 3,853,500 A * | 12/1974 | Gassmann et al. |
| 3,859,996 A | 1/1975 | Mizzy et al. |
| 3,894,663 A | 7/1975 | Carhart et al. |
| 3,977,574 A | 8/1976 | Thomas |
| 4,000,989 A * | 1/1977 | Dunegan |
| 4,022,207 A | 5/1977 | Citrin |
| 4,031,892 A | 6/1977 | Hurschman |
| 4,033,378 A | 7/1977 | Pauliukonis |
| 4,099,548 A | 7/1978 | Sturm et al. |
| 4,114,619 A | 9/1978 | Wagner |
| 4,139,008 A | 2/1979 | Wagner |
| 4,146,029 A | 3/1979 | Ellinwood, Jr. |
| 4,169,474 A | 10/1979 | Wagner |
| 4,284,077 A | 8/1981 | Wagner |
| 4,333,458 A | 6/1982 | Margulies et al. |
| 4,338,980 A | 7/1982 | Schwebel et al. |
| 4,393,870 A | 7/1983 | Wagner |
| 4,395,921 A | 8/1983 | Oppenlander |
| 4,398,930 A | 8/1983 | Larson et al. |
| 4,413,760 A | 11/1983 | Paton |
| 4,415,101 A | 11/1983 | Shapiro et al. |
| 4,425,121 A | 1/1984 | Young et al. |
| 4,435,173 A | 3/1984 | Siposs et al. |
| 4,444,560 A | 4/1984 | Jacklich |
| 4,457,712 A | 7/1984 | Dragan |
| 4,470,317 A | 9/1984 | Sabloewski et al. |
| 4,475,905 A | 10/1984 | Himmelstrup |
| 4,498,904 A | 2/1985 | Turner et al. |
| 4,526,294 A | 7/1985 | Hirschmann et al. |
| 4,529,401 A | 7/1985 | Leslie et al. |
| 4,538,616 A | 9/1985 | Rogoff |
| 4,573,970 A | 3/1986 | Wagner |
| 4,581,022 A | 4/1986 | Leonard et al. |
| 4,592,745 A | 6/1986 | Rex et al. |
| 4,596,556 A | 6/1986 | Morrow et al. |
| 4,600,403 A | 7/1986 | Wagner |
| 4,613,328 A | 9/1986 | Boyd |
| 4,659,327 A | 4/1987 | Bennett et al. |
| 4,664,128 A | 5/1987 | Lee |
| 4,676,781 A | 6/1987 | Phillips et al. |
| 4,680,027 A | 7/1987 | Parsons et al. |
| 4,710,172 A | 12/1987 | Jacklich et al. |
| 4,710,178 A | 12/1987 | Leonard et al. |
| 4,722,728 A | 2/1988 | Dixon |
| 4,743,299 A | 5/1988 | Chu |
| 4,790,824 A | 12/1988 | Morrow et al. |
| 4,820,287 A | 4/1989 | Leonard |
| 4,834,149 A | 5/1989 | Fournier et al. |
| 4,865,591 A | 9/1989 | Sams |
| 4,874,367 A | 10/1989 | Edwards |
| 4,883,472 A | 11/1989 | Michel |
| 4,913,699 A | 4/1990 | Parsons |
| 4,936,833 A | 6/1990 | Sams |
| 4,941,880 A | 7/1990 | Burns |
| 4,950,246 A | 8/1990 | Muller |
| 4,959,056 A | 9/1990 | Dombrowski et al. |
| 4,998,570 A | 3/1991 | Strong |
| 5,009,634 A | 4/1991 | Feldman et al. |
| 5,009,637 A | 4/1991 | Newman et al. |
| 5,024,656 A | 6/1991 | Gasaway et al. |
| 5,047,044 A | 9/1991 | Smith et al. |
| 5,050,612 A | 9/1991 | Matsumura |
| 5,064,413 A | 11/1991 | McKinnon et al. |
| 5,069,668 A | 12/1991 | Boydman |
| 5,085,642 A | 2/1992 | Sarnoff et al. |
| 5,092,842 A | 3/1992 | Bechtold et al. |
| 5,102,393 A | 4/1992 | Sarnoff et al. |
| 5,104,380 A | 4/1992 | Holman et al. |
| 5,112,317 A | 5/1992 | Michel |
| 5,114,406 A | 5/1992 | Gabriel et al. |
| 5,139,484 A | 8/1992 | Hazon et al. |
| 5,180,371 A | 1/1993 | Spinello |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,249,584 A | 10/1993 | Karkar et al. |
| 5,254,100 A | 10/1993 | Huband |
| 5,256,157 A | 10/1993 | Samiotes et al. |
| 5,267,977 A | 12/1993 | Feeney, Jr. |
| 5,279,294 A | 1/1994 | Anderson et al. |
| 5,279,584 A | 1/1994 | Dillard, III et al. |
| 5,279,585 A | 1/1994 | Balkwill |
| 5,279,586 A | 1/1994 | Balkwill |
| 5,330,430 A | 7/1994 | Sullivan |
| 5,342,309 A | 8/1994 | Hausser |
| 5,354,287 A | 10/1994 | Wacks |
| 5,372,634 A | 12/1994 | Monahan |
| 5,383,865 A | 1/1995 | Michel |
| 5,405,435 A | 4/1995 | Bekedam |
| 5,425,716 A | 6/1995 | Kawasaki et al. |
| 5,429,602 A | 7/1995 | Hauser |
| 5,445,620 A | 8/1995 | Haber et al. |
| 5,480,381 A | 1/1996 | Weston |
| 5,480,487 A * | 1/1996 | Figini et al. |
| 5,503,627 A | 4/1996 | McKinnon et al. |
| 5,508,975 A * | 4/1996 | Walter |
| 5,509,905 A | 4/1996 | Michel |
| 5,520,639 A | 5/1996 | Peterson et al. |
| 5,536,249 A | 7/1996 | Castellano et al. |
| 5,540,664 A | 7/1996 | Wyrick |
| 5,569,189 A | 10/1996 | Parsons |
| 5,584,416 A * | 12/1996 | Florian |
| 5,593,388 A | 1/1997 | Phillips |
| 5,593,390 A | 1/1997 | Castellano et al. |
| 5,630,796 A | 5/1997 | Bellhouse et al. |
| 5,649,912 A | 7/1997 | Peterson |
| 5,675,909 A | 10/1997 | Pare |
| 5,704,911 A | 1/1998 | Parsons |
| 5,713,873 A | 2/1998 | Jehle |
| 5,728,074 A | 3/1998 | Castellano et al. |
| 5,730,723 A | 3/1998 | Castellano et al. |
| 5,772,731 A * | 6/1998 | Harrison |
| 5,814,134 A * | 9/1998 | Edwards et al. |
| 5,820,602 A | 10/1998 | Kovelman et al. |
| 5,851,198 A | 12/1998 | Castellano et al. |
| 5,891,085 A | 4/1999 | Lilley et al. |
| 5,891,086 A | 4/1999 | Weston |
| 5,891,192 A | 4/1999 | Castellano |
| 5,893,397 A | 4/1999 | Peterson et al. |
| 5,899,880 A | 5/1999 | Bellhouse et al. |
| 5,925,021 A | 7/1999 | Castellano et al. |
| 5,957,166 A | 9/1999 | Safabash |
| 5,957,886 A | 9/1999 | Weston |
| 5,993,412 A | 11/1999 | Deily et al. |
| 6,063,053 A | 5/2000 | Castellano et al. |
| 6,080,130 A | 6/2000 | Castellano |
| 6,096,002 A | 8/2000 | Landau |
| 6,117,212 A * | 9/2000 | Buechele et al. |

| | | | | | | |
|---|---|---|---|---|---|---|
| 6,132,395 | A | 10/2000 | Landau et al. | FR | 1 445 659 | 6/1966 |
| 6,135,979 | A | 10/2000 | Weston | FR | 78 05814 | 3/1978 |
| 6,145,762 | A | 11/2000 | Orloff et al. | FR | 2 557 445 | 12/1984 |
| 6,149,625 | A | 11/2000 | Weston et al. | FR | 2 749 169 | 6/1996 |
| 6,156,008 | A | 12/2000 | Castellano | GB | 1 225 495 | 6/1967 |
| 6,168,587 | B1 | 1/2001 | Bellhouse et al. | GB | 1 574 267 | 2/1978 |
| 6,174,304 | B1 | 1/2001 | Weston | GB | 2 109 690 A | 2/1982 |
| 6,197,162 | B1 * | 3/2001 | Quiros | WO | 85/02546 A | 10/1984 |
| 6,309,371 | B1 | 10/2001 | Deboer et al. | WO | 89/08469 A1 | 3/1989 |
| 6,406,455 | | 6/2002 | Willis et al. | WO | 92/13583 A1 | 2/1992 |
| | | | | WO | 93/10838 | 11/1992 |
| | | | | WO | 95/03844 A1 | 7/1994 |
| | | | | WO | 96/19252 A1 | 12/1995 |
| | | | | WO | 96/28202 A1 | 3/1996 |
| | | | | WO | 97/13537 A1 | 10/1996 |
| | | | | WO | 97/25015 A1 | 1/1997 |
| | | | | WO | WO 9722375 A | 6/1997 |
| | | | | WO | WO 9738775 A | 10/1997 |

FOREIGN PATENT DOCUMENTS

| | | |
|---|---|---|
| EP | 0 327 910 A2 | 1/1989 |
| EP | 0 347 190 A1 | 6/1989 |
| EP | 0 368 191 A1 | 11/1989 |
| EP | 0 416 975 A1 | 8/1990 |
| EP | 0 427 457 A2 | 11/1990 |
| FR | 1 149 735 | 12/1957 |
| FR | 1 170 312 | 1/1959 |

* cited by examiner

SYSTEM AND METHOD FOR REMOVING DISSOLVED GAS FROM A SOLUTION

FIELD OF THE INVENTION

This invention relates to a system and multiple methods for removing gas from an aqueous solution, and in particular, embodiments for avoiding subdermal hematomas from the use of a needle-less injector when the system and methods are employed in conjunction with the loading of a needle-less injector ampoule.

BACKGROUND OF THE INVENTION

In an application in which a liquid must be filled into a sealed container, it may be preferable that substantially all gas be removed from the liquid either prior to filling or soon after the container is filled. For example, in filling ampoules with liquid medications for use in a needle-less injector, it may be desirable to de-gas the medication prior to filling the ampoule or, alternatively, for the medication to be de-gassed once the ampoule is filled.

Typically, needle-less medication injections are performed with "permanent gun" instruments, generally referred to as "jet injectors." These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. This method of medication delivery is referred to as a subcutaneous injection.

Medication delivery via needle-less injector periodically results in the formation of subdermal hematomas, and efforts have been made to reduce the likelihood and severity thereof. In U.S. Pat. No. 6,156,008 issued Dec. 5, 2000, we described an injection site detecting device for avoiding subdermal hematomas from an injection, wherein the detecting device is employed prior to injection to locate a site of low blood flow, relative to the surrounding area. Since it is believed that administering a needle-less injection in a region of lower blood flow corresponds to lower bruising potential, utilization of this device reduces the likelihood of causing a subdermal hematoma from administration of an injection with a needle-less injector.

Subdermal hematomas, tissue damage, and scarring from mechanical force injury may also result from the use of needle-less injectors when pockets of gas are present in the injector ampoule prior to dispensing the medication contained therein. Within the 800 to 1200 fps range, optimal for acceleration of liquid medication through the skin via a needle-less injector, liquid readily penetrates the skin while air does not. Thus, gas pockets accelerated against the skin lead to the formation of a bruise and can be quite painful for the recipient, whereas liquid medication passes into and/or through the skin without discomfort.

In general, the gas pocket is found at the dispensing terminus of the ampoule, which is proximate to the skin, though this can change depending on the orientation of the ampoule during storage. Further, when the cap is removed from the end of a needle-less injector, exposing the dispensing area for application to the skin surface, any gas pocket not already situated at the dispensing end may tend to migrate toward that end, due to the pressure change caused by cap removal. This motion of the gas pocket often forces some liquid from the ampoule, thereby diminishing the volume of liquid that will be injected into the recipient. This renders the dosage level inaccurate, as a nontrivial volume of medication is lost from the injector prior to use.

Gas pockets may be present from the outset, resulting from the improper loading of an ampoule. Filling the ampoule with an insufficient amount of liquid clearly leaves such a pocket. However, overfilling the ampoule and removing any excess to arrive at the desired volume is generally not a practical alternative, either, since it is likely that a small amount of liquid will remain on the outer surface of the ampoule. In the medical context, any such liquid is likely to foster the growth of bacteria, which is unacceptable in a scenario where sterile conditions are imperative. Any ampoule with such bacterial growth must be disposed of, and is therefore wasteful.

Even in a perfectly filled ampoule, where no cognizable gas pockets are present immediately following loading, pockets may still develop over time as the dissolved gases present in the liquid separate out from solution. Dissolved gases are naturally present in liquids as a function of the gases' partial pressures in the local atmosphere. Known to those skilled in the art as Henry's Law, the concentration of a particular gas in solution is proportional to the pressure of that same gas in the air abutting the solution. Thus, dissolved gases are present in the liquids filled into ampoules under normal conditions (i.e., wherein filling is not performed in a vacuum, or the like) in concentrations proportional to their partial pressure in air. These dissolved gases consist mostly of nitrogen and oxygen, along with several trace gases, and are found latent in the solution in amounts related to their partial pressures in the local atmosphere.

The size of gas pockets varies according to the pharmaceutical active in solution, as some actives allow liquid to retain greater amounts of gas than others, but in some instances a pocket may be as large as 20% of the total ampoule volume. This naturally occurring formation of gas pockets is exacerbated when pre-filled ampoules remain unused for substantial periods of time. Again, varying with the type of active in solution, some actives will form substantial gas pockets after only a few days, while others may not form a pocket for a year or more. For certain medicaments, an ampoule may be stored as long as three to five years, and nearly every active will generate a gas pocket in that amount of time.

Increased temperature also affects the separation of gas from solution, prompting gas pockets to form faster and larger. Pharmaceutical actives generally require storage within a certain optimal temperature range in order to prevent the active from breaking down and thus losing efficacy. For example, many proteins suitable for injection will denature at high temperatures. However, optimal temperature ranges for efficacy may not have any correlation with temperature that would avoid a gas pocket from forming in storage. Thus, one may be forced to choose between either preserving drug efficacy or minimizing gas pocket formation.

In the context of injection by more traditional means such as with a preloaded syringe, it is well established that any significant amount of air in such a device will cause pain for the recipient and potentially far more dire consequences if the amount of air is substantial. Gas pockets may develop in these syringes much in the way described above with regard to ampoules of needle-less injectors, as these devices are frequently subject to similar storage conditions and requirements. Those administering such injections can more readily obviate these limitations, however, as air may be evacuated from the liquid-containing chamber of a syringe by partially depressing the plunger while the syringe is inverted immediately prior to administration of an injection. This is generally not possible with a needle-less injector, as the entire volume of a needle-less injector ampoule is evacuated in one step during normal operation. Moreover, liquid that is inadvertently evacuated from the chamber of a syringe along with the undesirable air does not present a sterility concern, since bacteria will not grow in a pharmacologically hazardous amount in the few moments between evacuating such air and administering an injection. Oftentimes some small quantity of air will remain in the syringe chamber, however, resulting in an injection more painful than would have been had the air been removed by another, more thorough methodology.

SUMMARY OF THE DISCLOSURE

It is an object of an embodiment of the present invention to provide a method for removing gas from an aqueous solution.

It is an object of another embodiment of the present invention to provide a method for filling a container with a de-gassed liquid, wherein the liquid contains gas prior to being filled into the container.

It is an object of another embodiment of the present invention to provide a method for filling a container with liquid containing a gas wherein the gas separates out from the liquid such that the liquid becomes de-gassed.

It is an object of yet another embodiment of the present invention to provide a method for avoiding subdermal hematomas in the course of administering needle-less injections, that obviates for practical purposes, the above-mentioned limitations.

The present invention relates to a system and multiple methods for removing dissolved gases from a liquid to be filled into a container that is subsequently filled as well as methods for removing gases from a liquid after a container is filled. One embodiment of the instant invention involves partially filling a tank with gas-containing liquid and applying a vacuum source to an opening in the tank so that the atmospheric pressure above the gas-containing liquid is significantly reduced. In particular embodiments of the invention, the tank may be rotated to facilitate consistent removal of dissolved gases throughout the liquid. In alternative embodiments, the tank may be heated to further facilitate the gas removal process. Once the desired amount of dissolved gas has been removed, the vacuum source may be removed from the tank opening and the tank may be sealed. The tank may then be turned upside down so that the de-gassed liquid is near the opening and the tank may be coupled to filling equipment. Filling equipment may then be used to fill a container, such as the ampoule of a needle-less injector, a syringe, or the like.

The device in this embodiment operates as a function of what is known to those skilled in the art as Henry's Law, which states that the pressure of a gas abutting a solution is proportional to the concentration of the same gas dissolved in the solution. Thus, as the air pressure in the tank of the present invention is reduced, the concentration of the gases in the solution decreases accordingly. In this embodiment of the present invention, these gases consist mostly of nitrogen and oxygen, and are found latent in the solution in amounts related to their partial pressure in the local atmosphere. However, the system will function in substantially the same manner with other dissolved gases.

Another embodiment of the instant invention involves partially filling a tank with gas-containing liquid and heating the tank. The liquid in the tank is either boiled or warmed to a temperature below its boiling point, while the tank remains open. Once the desired amount of dissolved gas has been removed, the tank opening may be sealed. The tank may then be turned upside down so that the de-gassed liquid is near the opening and the tank may be coupled to filling equipment. Filling equipment may then be used to fill a container, such as the ampoule of a needle-less injector, a syringe, or the like.

Yet another embodiment of the instant invention involves partially filling a tank with gas-containing liquid and resonating sound waves through the liquid, where such waves are originated by the high frequency oscillations at the tip of a device deployed therein. Known to those skilled in the art as "sonicating," such a device agitates a liquid and removes gas therefrom, while no harm is caused to a solute dissolved therein. This device may be employed in conjunction with a vacuum, heat, or a combination thereof. Once the desired amount of dissolved gas has been removed, the tank opening may be sealed. The tank may then be turned upside down so that the de-gassed liquid is near the opening and the tank may be coupled to filling equipment. Filling equipment may then be used to fill a container, such as the ampoule of a needle-less injector, a syringe, or the like.

Yet another embodiment of the instant invention involves filling a vacuum-sealed bag with lyophilized solute, or another solute in either liquid or solid form. De-gassed water or another appropriate de-gassed solvent may then be added to the bag, with the resulting solution being substantially free of dissolved gas. The bag can then be coupled to filling equipment and used to fill a container, such as the ampoule of a needle-less injector, a syringe, or the like.

Yet another embodiment of the instant invention involves partially filling a tank with gas-containing liquid and percolating another gas through the liquid. Concurrently, a vacuum is applied to the interior atmosphere of the tank such that a portion of the percolating gas is removed, along with a portion of the gas that was formerly dissolved in the liquid. The rate of addition of percolating gas to the system may be less than, equal to, or greater than the rate at which gas is removed from the tank via the vacuum source, such that a user may additionally utilize a pressure differential to drive gas out of the liquid. Once the desired amount of dissolved gas has been removed from the liquid, displaced by the percolating gas, the vacuum source and percolating gas line may be removed from the tank and the tank may be sealed. The tank may then be turned upside down so that the percolating gas-containing liquid is near the opening and the tank may be coupled to filling equipment. Filling equipment may then be used to fill a container, such as the ampoule of a needle-less injector, a syringe, or the like. The percolating gas may remain dissolved in the liquid after a container is filled therewith. Of the two types of preferred percolating gases, one type diffuses out of the container directly through the walls thereof, while the other type bonds or otherwise chemically reacts with a part of the container or other mechanical structure in contact with the liquid or chemical lining on the interior of the container, such that the gas extracts itself from the liquid. Preferably, the gas does not change phase during this bonding or other reaction.

Yet another embodiment of the instant invention involves "salting out" the dissolved gas from a liquid to be filled into a container. Along with any desirable solute, a salt or buffer is added to a liquid at a sufficiently high concentration such that substantially no gas can remain in the concentrated solution. The solution can be filled via filling equipment into a container, such as the ampoule of a needle-less injector, a syringe, or the like. The solution can further be diluted with de-gassed water or another suitable de-gassed liquid either prior to filling into a container, immediately after filling into a container, or at a later time such as just before administration of an injection with a needle-less injector.

Yet another embodiment of the instant invention involves a process similar to "salting out," however in this embodiment the solute itself (e.g., a pharmaceutical active) is present in the liquid in such a high concentration that substantially no gas can remain in the liquid. The solution can be filled via filling equipment into a container, such as the ampoule of a needle-less injector, a syringe, or the like. The solution can further be diluted with de-gassed water or another suitable de-gassed liquid either prior to filling into a container, immediately after filling into a container, or at a later time such as just before administration of an injection with a needle-less injector.

Yet another embodiment of the instant invention involves an absorbent material being held in a compartment external to the container, where only gaseous communication exists between this compartment and the interior of the container. The liquid contains a gas that is absorbed by the material contained in the compartment, such that the liquid de-gasses after the container is filled.

DETAILED DESCRIPTION OF THE PREFERRED EMBODIMENTS

Figure 1A:
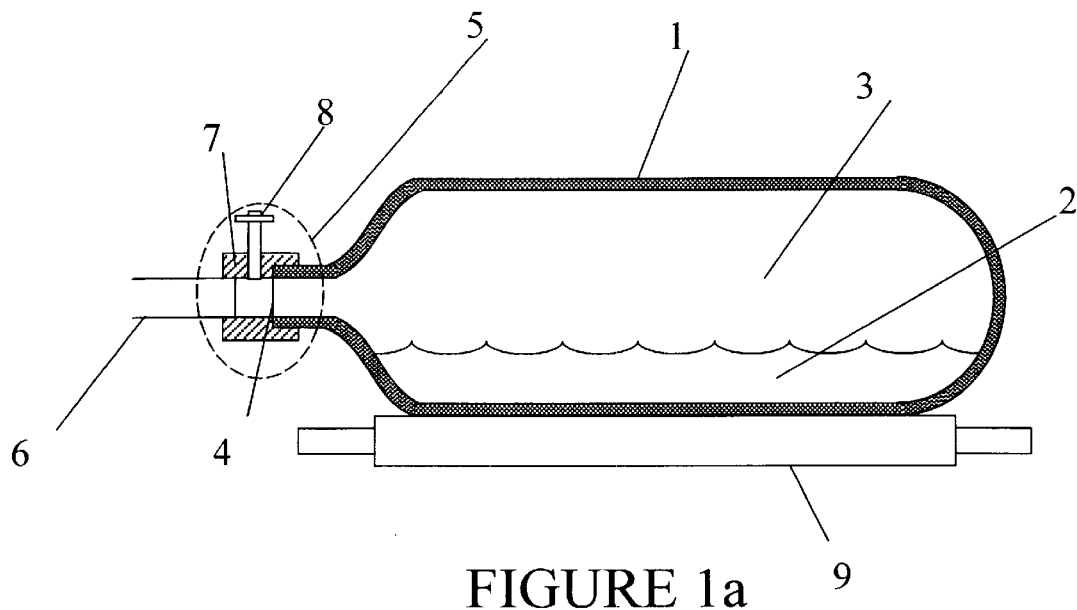
FIG. 1a illustrates a cross-section of an assembly that may be used in an embodiment of the de-gassing system according to the present invention wherein rollers are incorporated therein.

As shown in the drawings for purposes of illustration, the invention is embodied in a system and several methods for removing dissolved gas from a solution. In preferred embodiments of the present invention, the system and methods are for avoiding or minimizing subdermal hematomas (bruising) from a needle-less injection and for avoiding the formation of a gas pocket in a container filled with liquid. The system and methods may be used in conjunction with a needle-less injector, such as those disclosed in U.S. Pat. No. 5,730,723 issued Mar. 24, 1998, U.S. Pat. No. 5,851,198 issued Dec. 22, 1998, and U.S. Pat. No. 6,063,053 issued May 16, 2000, which are herein incorporated by reference in their entirety.

The liquids appropriate for use in accordance with the system and methods of the instant invention may be chosen from any gas-containing liquids. In preferred embodiments, the liquid is selected from those appropriate for injection with a syringe or needle-less injector. Such liquids may include, but are not limited to, vaccines, injectable medications, pharmaceutical agents, and the like. Preferably, the molecular weight of a solute dissolved in the liquid is in the range of from about 1 to about 500,000 Daltons. Accordingly, in preferred embodiments, the viscosity of the liquid is in the range of from about 0.2 to about 10 Centipoise. More preferably, the viscosity of the liquid is in the range of from about 0.4 to about 2.0 Centipoise.

In a first embodiment, FIG. 1a depicts a system that may be used to remove dissolved gas according to an embodiment of the invention. Preferably, the system is employed in a room of substantially constant temperature, set as is appropriate for the particular liquid that is to be degassed. The tank 1 holds the liquid 2 from which the dissolved gas is to be removed. The tank 1 may be of any convenient size, ranging in preferred embodiments from several liters to a one hundred-gallon drum or larger, depending on the scale of production. The tank 1 may only be partially filled with gas-containing liquid 2 so that the tank 1 also contains an interior atmosphere 3. The tank 1 may be filled to any suitable capacity, though in preferred embodiments it may be initially filled to approximately 85% to 90% of total tank volume. The tank 1 may have an opening 4 through which the liquid 2 is loaded in its gas-containing state (i.e., containing the dissolved gas to be removed). The tank 1 may be made of stainless steel so that no gas may escape or enter the interior atmosphere 3 through the wall of the tank 1. The tank may be sterilized prior to filling with the gas-containing liquid 2.

The opening 4 may be sealed so as to be fluid and/or airtight with a sealing mechanism 5, such as a ball or poppet valve. The sealing mechanism 5 may be chosen so that its open and closed states are selectable and that the closed state is the default (i.e., no force need be applied or action taken to maintain the closed state).

The empty tank 1 may initially be filled, preferably in the upright position (i.e., with opening 4 at top), with gas-containing liquid 2 by placing the sealing mechanism 5 in its open state and connecting a source of gas-containing liquid to the opening 4 or the sealing mechanism 5 so that the liquid 2 may flow into the tank 1. The sealing mechanism 5 may then be put in the closed state and the source of gas-containing liquid may be disconnected from the opening 4 and replaced with a gas removal source 6. The gas removal source 6 may be a vacuum pump coupled to the opening 4 by vacuum tubing. The tank may be oriented so as to maximize the surface area of the interface between the liquid 2 and the interior atmosphere 3. For example, in the embodiment shown in FIG. 1a, the tank 2 is shown laid on its side.

The vacuum source may remove gas from the interior atmosphere 3. As the pressure of the gas contained in the interior atmosphere 3 drops below local atmospheric pressure (generally about 1 atm), the amount of gas dissolved in the liquid 2 will drop correspondingly. If a 98% vacuum is applied to the interior atmosphere 3 for a sufficient time (e.g., about ten minutes) to allow the liquid to reach an equilibrium state, then approximately 98% of the dissolved gas should be removed from the liquid 2 based on Henry's Law, as described above.

The tank 1 may be generally cylindrical in shape and may be slowly rolled (e.g., from about 1 to about 6 rpm) to expose more of the liquid 2 to the interior atmosphere 3 via rollers 9. Rollers 9 may further contain a heating element therein, such that the liquid 2 might be warmed and rolled simultaneously, while the vacuum is applied thereto. Alternatively, a heating element might be included in addition to rollers 9, or the rollers 9 might be heated prior to the tank 1 being placed thereon. In each instance, the liquid 2 may be heated during application of the vacuum. Heating the liquid 2 may facilitate removal of gas from solution, and may be performed at any appropriate temperature, though it is preferable that the liquid 2 is heated at a temperature beneath its boiling point. Where a protein is in solution, however, heating is preferably not performed above 80° C., since such elevated temperatures greatly increase the potential for bacterial growth and multiplication. The vacuum may be applied until no additional gas is being removed from the liquid 2.

The sealing mechanism 5 may then be put in the closed position and the gas removal source 6 is disconnected from the opening 4 or sealing mechanism 5. As shown in the embodiment depicted in FIG. 1a, the sealing mechanism 5 may include a cap 7 and a valve assembly 8 (such as a stopcock, stem valve, or ball valve). The cap 7 and valve assembly 8 may be coupled together. The cap 7 may be screwed on to the outer surface of the opening 4 of the tank 1, using a ring of TEFLON (polytetrafluoroethylene) or other suitable material to ensure an airtight seal between the cap 7 and the opening 4. Moreover, the interface between the cap 4 and the valve assembly 8 may be lined with TEFLON (polytetrafluoroethylene) or another suitable material to maintain an airtight seal.

Depending on the efficiency of the vacuum source, it may be necessary to repeat this process to remove the desired amount of dissolved gas from the liquid 2. For example, if a 98% vacuum is applied, approximately 2% of the dissolved gas will remain after each round of evacuation. To remove a greater amount of the dissolved gas, after each round of evacuation, the tank 1 may be removed from the rollers 9 and, with the sealing mechanism 5 in the closed state and the gas removal source 6 disconnected, may be set aside for a short period (e.g., less than about 1 hour) to stabilize. Upon stabilization, the gas removal source 6 may be reconnected and another evacuation round may commence, removing another 98% of the remaining dissolved gas. With sufficient repetition, it may be possible to achieve 99.9% removal of the dissolved gas. The removal of gas, especially where heating is involved, may include removal of a certain amount of water vapor, which may be undesirable. To correct for the undesirable removal of water vapor, de-gassed water may be added to the liquid 2 to correct the concentration and volume of the liquid 2. Alternatively, the initial concentration of medicament or other solute in the liquid 2 may be made lower than that which is desirable after de-gassing, such that removal of water vapor from the liquid 2 will result in an appropriate concentration.

Once the desired amount of dissolved gas has been removed from the liquid 2, and any appropriate adjustments made to the concentration of a solute present in the liquid 2 by addition of de-gassed water, the tank 1 may be suspended with the opening 4 facing downward. The interior atmosphere 3 may be substantially evacuated.

Figure 2:
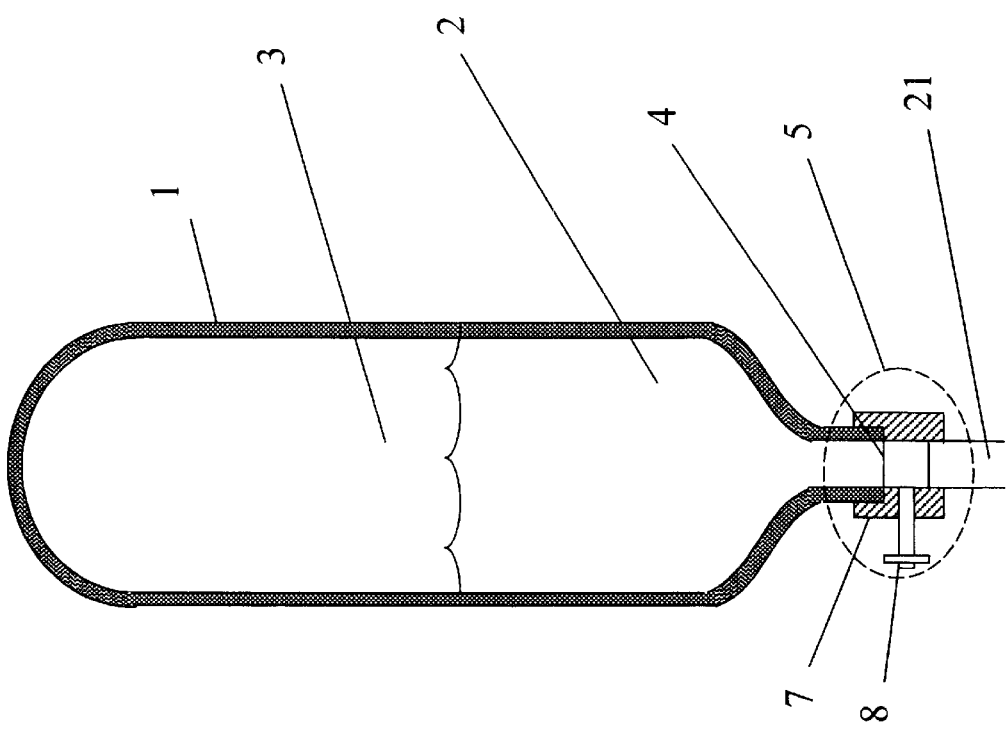
FIG. 2 illustrates a cross-section of a tank containing de-gassed liquid for use in a filling machine.

As depicted in FIG. 2, a filling supply line 21 may be coupled to the opening 4 so that degassed liquid 2 may be transferred to any suitable container via filling equipment (not shown). The filling equipment may be coupled to the filling supply line 21. In order to accomplish transfer of the de-gassed liquid 2 through the filling supply line 21, the pressure difference between the vacuum in the interior atmosphere 3 and the opening 4 may be overcome by the force of gravity and/or suction force applied via the filling equipment and filling supply line 21.

Figure 1B:
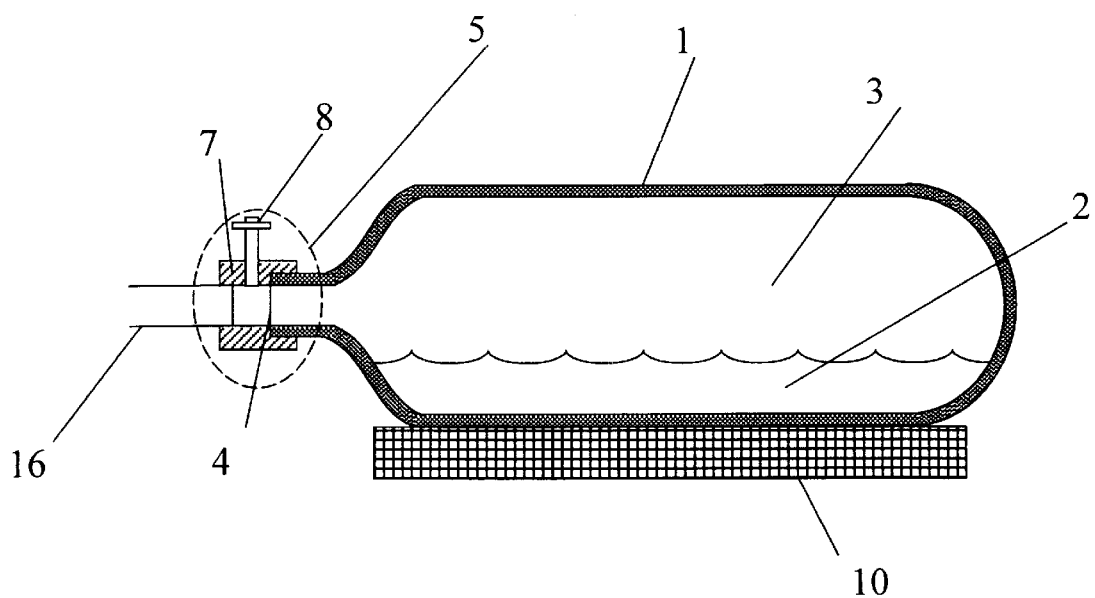
FIG. 1b illustrates a cross-section of a similar assembly wherein a heating element is incorporated therein.

In a second embodiment, as depicted in FIG. 1b, gas removal may be accomplished by heating the liquid contained in the tank 1. In this embodiment, the system includes a heating element 10. The tank 1 may be heated while resting on its side, as depicted in FIG. 1b, or in the upright position (not shown). The tank is prepared and filled with gas-containing liquid 2 in accordance with the methods set forth in the first embodiment above, yet preferably no vacuum source 6 is applied.

For those liquids 2 containing pharmaceutical actives or other solutes that can survive boiling, or for liquids 2 which are solute-free, or where boiling is otherwise desirable, the tank 1 may be heated until the temperature is such that the liquid 2 boils. Boiling may remove substantially all of the gas previously dissolved in the liquid 2. Boiling may be performed with the sealing mechanism 5 in the open state, to allow gas released from the liquid 2 to escape from the interior atmosphere 3 of the tank 1, and may be continued until substantially all of the dissolved gas is removed from the liquid 2.

For those liquids 2 containing pharmaceutical actives or other solutes that cannot survive boiling, or where boiling is otherwise undesirable, the liquid 2 contained in the tank 1 may be warmed to a temperature below the boiling point of the liquid 2. Warming may also be performed with the sealing mechanism 5 in the open state, to allow gas released from the liquid 2 to escape from the interior atmosphere 3 of the tank 1, and may be continued until substantially all of the dissolved gas is removed from the liquid 2.

Once substantially all gas has been removed from the liquid 2 either by either boiling or warming, the sealing mechanism 5 may be closed and a removal line 16 may be coupled to the sealing mechanism 5 as depicted in FIG. 1b. It may be desirable to cool the liquid 2 prior to filling. The bag containing the de-gassed liquid may then be coupled to filling equipment (not shown).

Figure 10:
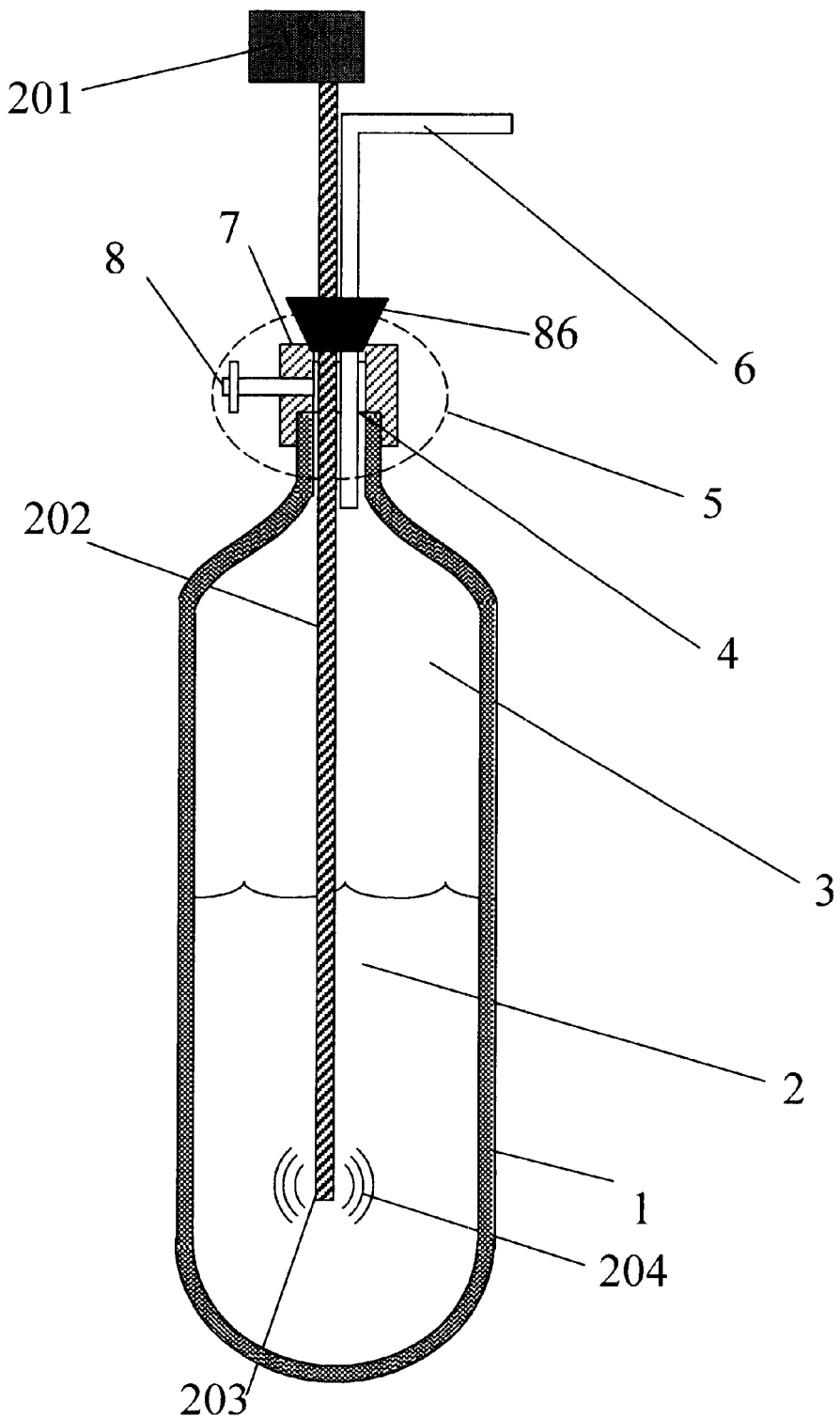
FIG. 10 illustrates a cross-section of an assembly that may be used in an embodiment of the de-gassing system according to the present invention, wherein sonicating device is incorporated therein.

In a third embodiment, as depicted in FIG. 10, a sonicating device 201 may be employed, wherein a sonicating rod 202 may be immersed in said liquid 2 within a tank 1, and gas removal may be achieved by sending sound waves 204 through the liquid 2, as depicted in FIG. 10. A vacuum source 6 or a heating element (not shown) may be applied as well. Sound waves 204 may be generated by the high frequency oscillation of a tip segment 203 of a rod 202 of a sonicating device 201.

The empty tank 1 may initially be filled, preferably in the upright position (i.e., with opening 4 at top), with gas-containing liquid 2 by placing the sealing mechanism 5 in its open state and connecting a source of gas-containing liquid to the opening 4 or the sealing mechanism so that the liquid 2 may flow into the tank 1. The sealing mechanism 5 may then be put in the closed state and the source of gas-containing liquid may be disconnected from the opening 4 and replaced with a splitter device 86 that is further coupled to a rod 202 of a sonicating device 201, and a gas removal source 6. The gas removal source 6 may be a vacuum pump coupled to the opening 4 by vacuum tubing.

Once substantially all gas has been removed from the liquid 2, the sealing mechanism 5 may be closed and a removal line 16 may be coupled to the sealing mechanism 5 as depicted in FIG. 1b. The tank 1 containing the de-gassed liquid may then be coupled to filling equipment (not shown).

In a fourth embodiment, water or another appropriate solvent may be de-gassed by vacuum removal of gas therefrom as described in the first embodiment above or by heating as described in the second embodiment above, or any other appropriate means. Once substantially all gas has been removed from the water or other solvent, the sealing mechanism 5 of the tank 1 depicted in FIGS. 1a and 1b may be closed and a removal line 16, as depicted in FIG. 1b may be coupled to the sealing mechanism 5.

Figure 9A:
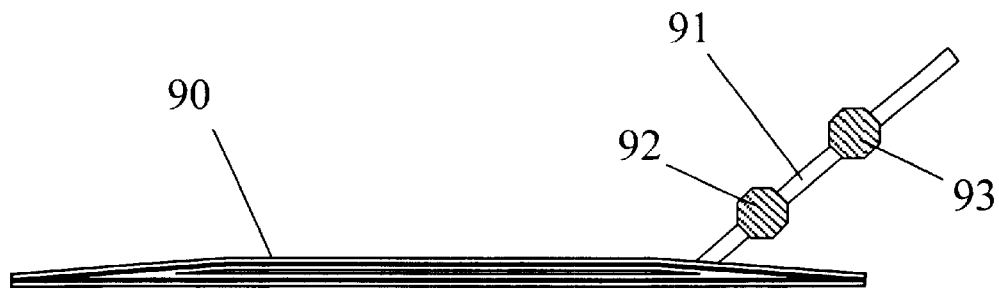
FIG. 9a illustrates a cross-section of an air-free bag that may be used in an embodiment of the de-gassing system according to the present invention.

As depicted in FIG. 9a, the removal line 16 is further coupled to a bag input line 91, which is coupled to a bag 90, made from a substantially air-impermeable material such as MYLAR (polyethylene terephthalate polyester film), though any similar appropriate vessel may be used. The bag 90 is preferably substantially free of air, and may be preloaded with a predetermined amount of a lyophilized pharmaceutical active or other solute, preferably in solid form, though the preloaded active may alternatively be in the form of a de-gassed solution. The bag input line 91 may be fitted with a primary clamp 92, and further may be fitted with a secondary clamp 93. Filling of a bag 90 is preferably performed in accordance with practices similar to those in filling bags with intravenous drugs or blood.

Figure 9B:
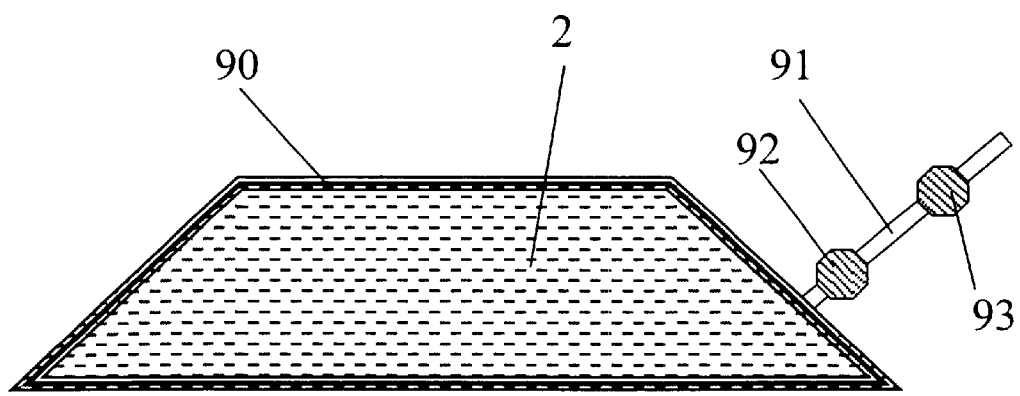
FIG. 9b illustrates a cross-section of a bag that may be used in an embodiment of the de-gassing system according to the present invention once the bag is filled with de-gassed liquid.

Once the removal line 16 and bag input line 91 are coupled together, the bag 90 may be filled with liquid 2. The sealing mechanism 5 may be opened and the liquid (e.g., de-gassed water or other de-gassed solvent) 2 may be loaded into the bag. The liquid 2 and the solute may mix within the bag to form a de-gassed solution, as depicted in FIG. 9b. When the volume of the bag 90 reaches a predetermined capacity, the primary clamp 92 may be closed to form an airtight seal. A secondary clamp 93 may be sealed as well. The bag may then be coupled to filling equipment (not shown).

Figure 8A:
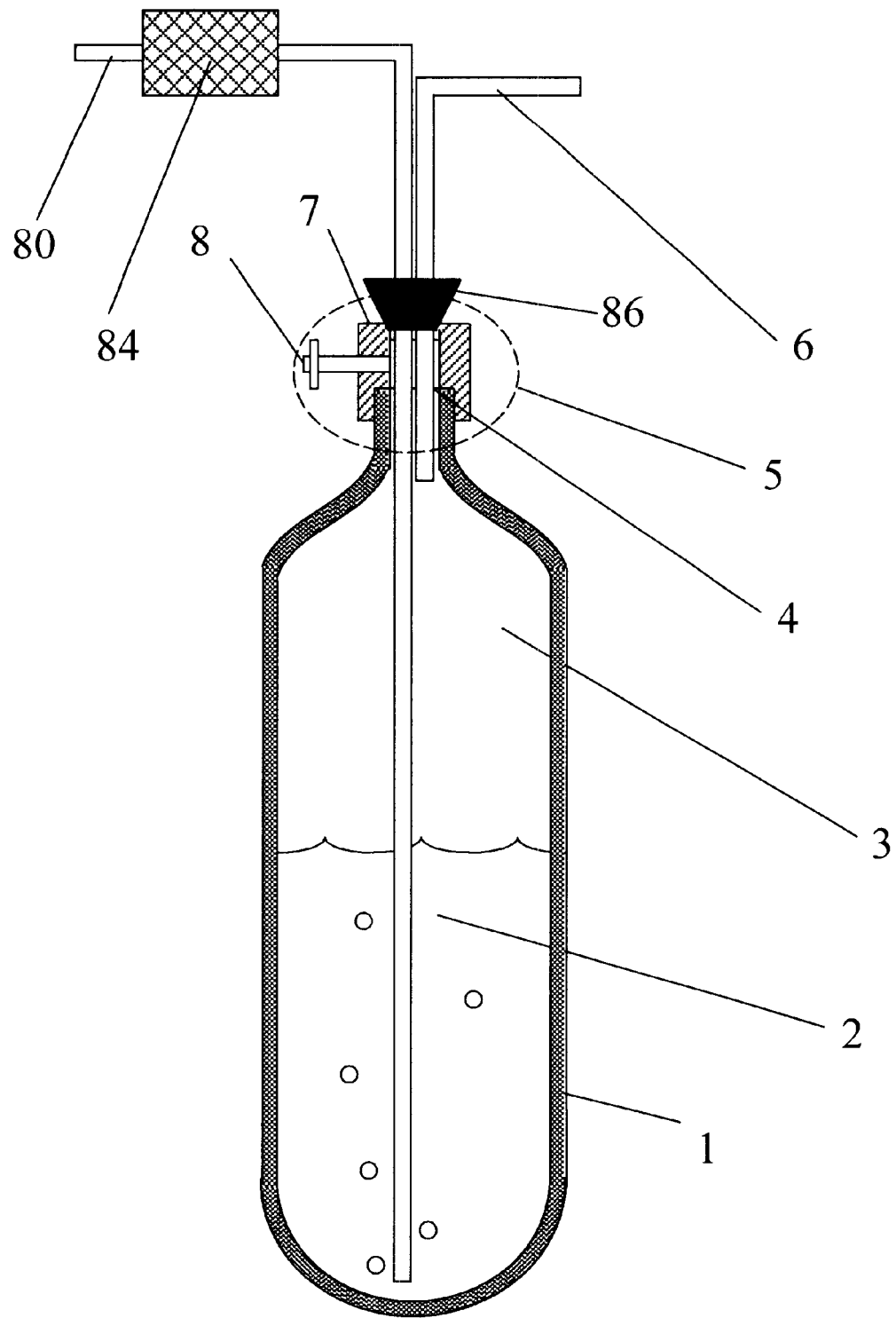
FIG. 8a illustrates a cross-section of an assembly that may be used in an embodiment of the de-gassing system according to the present invention, wherein a percolating gas line is incorporated therein.

In a fifth embodiment, FIG. 8a depicts a system that may be used to remove dissolved gas according to an embodiment of the invention. Preferably, the system is employed in a room of substantially constant temperature, and this temperature is set as is appropriate for the particular liquid that is to be de-gassed. The tank 1 holds the liquid 2 from which the dissolved gas is to be removed. The tank 1 may be of any convenient size, ranging in preferred embodiments from several liters to a one hundred-gallon drum or larger, depending on the scale of production. The tank 1 may only be partially filled with gas-containing liquid 2 so that the tank 1 also contains an interior atmosphere 3. The tank 1 may be filled to any suitable capacity, though in preferred embodiments it may be initially filled to approximately 80% to 95% of total tank volume. The tank 1 may have an opening 4 through which the liquid 2 is loaded in its gas-containing state (i.e., containing the dissolved gas to be removed). The tank 1 may be made of stainless steel so that no gas may escape or enter the interior atmosphere 3 through the wall of the tank 1. The tank may be sterilized prior to filling with the gas-containing liquid 2.

The opening 4 may be sealed so as to be fluid and/or airtight with a sealing mechanism 5, such as a ball or poppet valve, similar to that described in accordance with the first embodiment above. The opening 4 may further be fitted with a splitter device 86 that allows both a percolating gas line 80 and a gas removal source 6 to be simultaneously inserted through opening 4 in an airtight fashion.

Figure 8B:
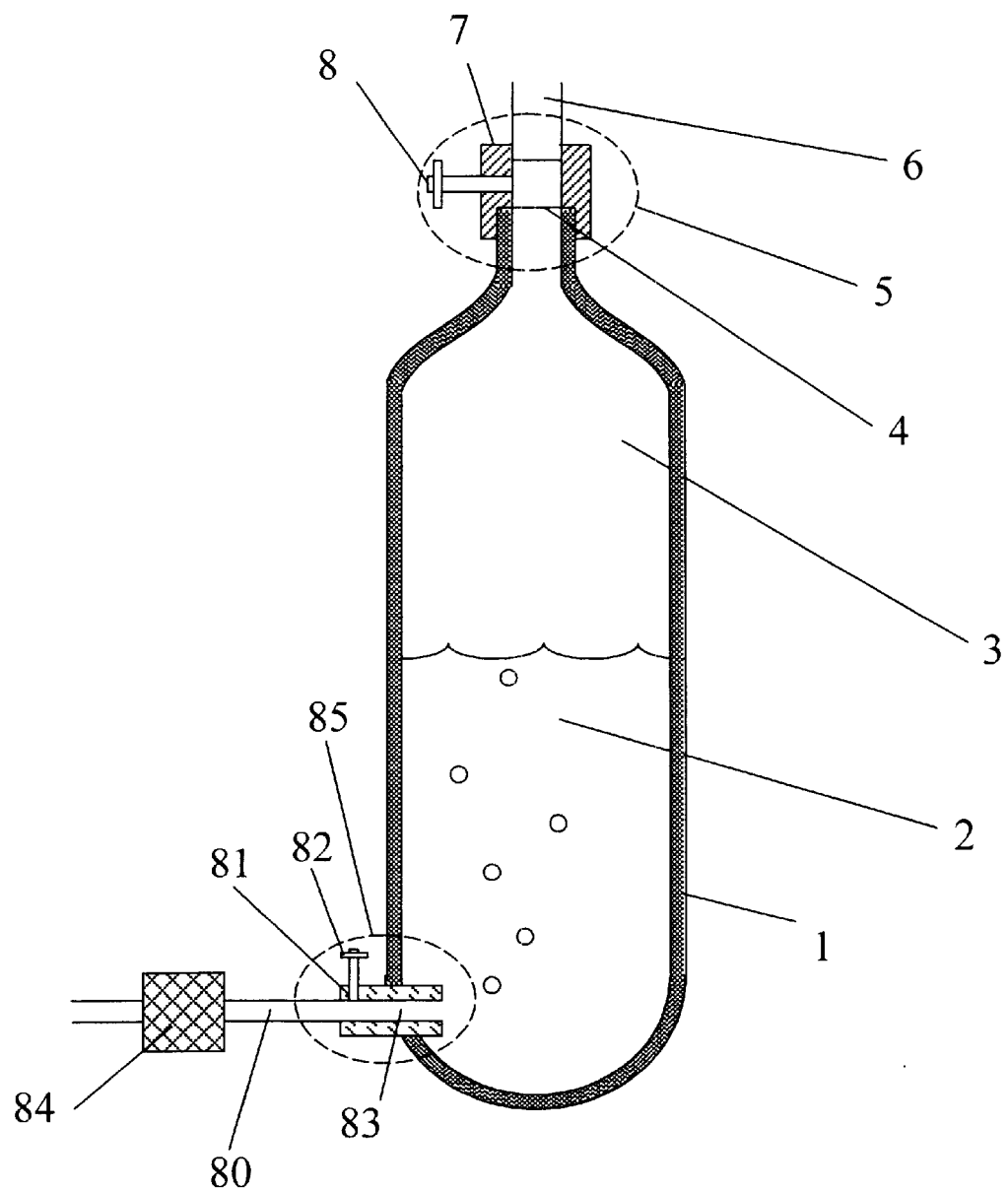
FIG. 8b illustrates a cross-section of an assembly that may be used in an embodiment of the de-gassing system according to the present invention wherein a percolating gas line is incorporated in a second opening of the tank.

Alternatively, as depicted in FIG. 8b, the tank 1 may have a second opening 83 through which a percolating gas may be forced via percolating gas line 80 through the fluid 2 in the tank 1. Similar to the opening 4, the second opening 83 may be sealed so as to be fluid and/or airtight with a sealing mechanism 85 such as, for example, a cap 81 and valve assembly 82.

The empty tank 1 may initially be filled, preferably in the upright position (i.e., with opening 4 at top), with gas-containing liquid 2 by placing the sealing mechanism 5 in its open state and connecting a source of gas-containing liquid to the opening 4 or the sealing mechanism 5 so that the liquid 2 may flow into the tank 1. The sealing mechanism 5 may then be put in the closed state and the source of gas-containing liquid may be disconnected from the opening 4 and replaced with a splitter device 86 that is further coupled to percolating gas line 80 and gas removal source 6, as in the embodiment depicted in FIG. 8a, or replaced solely with a gas removal source 6, as in the embodiment depicted in FIG. 8b. The gas removal source 6 may be a vacuum pump coupled to the opening 4 by vacuum tubing.

The gas removal source 6 may remove gas from the interior atmosphere 3 concurrently with the addition of a percolating gas through a gas line 80, which may first pass through a humidifier 84 prior to being forced into the tank 1. The inclusion of a humidifier 84 may obviate the loss of water vapor from the liquid 2. Preferably, the percolating gas forced through the gas line 80 is a small, inert gas, or a self-extracting gas.

The small, inert gas of this embodiment is selected for its ability to permeate the wall of a container into which the liquid 2 is to be later filled. Thus, the liquid 2 may contain gas upon filling into the container, but this same gas will diffuse out of the liquid 2, through the container wall, and into the local atmosphere. In preferred embodiments, this percolating gas is a small, inert gas such as helium, which readily travels through such materials as plastics, glass, and other suitable materials.

Self-extracting gases are defined for purposes of the instant invention as those gases that may chemically react with another material, with or without changing phase, once the liquid containing these gases is filled into a container, such that the gases extract themselves from the liquid. For example, the material comprising the wall of the container to be filled or another element of the container which contacts the liquid 2 (such as the plunger of a needle-less injector), or a chemical lining on the interior of the container might be comprised, at least in part, of a material that may react with such a self-extracting gas. In such chemical reactions, the selfextracting gas bonds with the material, is absorbed by the material or otherwise reacts therewith such as to remove itself from the liquid. Preferably, the self-extracting gas bonds to material comprising the wall of the container without changing phase during the chemical reaction (i.e., the percolating gas remains in the gas phase, yet bonds to the container wall material).

In operation, the percolating gas may be percolated into the tank 1, through liquid 2 and into interior atmosphere 3. Some of the percolating gas may collect in the interior atmosphere 3, while the remainder of the percolating gas may dissolve in the liquid 2. The dissolved percolating gas may displace the gas previously dissolved in the liquid 2, forcing it into the interior atmosphere 3. The gas removal source 6 may then draw both the previously dissolved gas as well as a portion of the percolating gas out of the tank 1 at the same rate at which percolating gas is added to the tank 1. Only a portion of said percolating gas may be removed, as the remainder of said percolating gas may remain in solution in the liquid 2. This process may be continued until substantially all of the previously dissolved gas is forced out of the liquid 2, having been displaced by a volume of percolating gas that remains in said liquid 2.

Alternatively, the input rate of the percolating gas may be either less or greater than the rate of removal of gas from tank 1. When the input rate is less than the rate of removal, a negative pressure differential may be created such that the pressure in the interior atmosphere 3 drops below local atmospheric pressure. The amount of total gas dissolved in the liquid 2 (gas previously dissolved in liquid 2 as well as percolating gas) may drop correspondingly, in accordance with Henry's Law, as discussed above, facilitating the removal of both previously dissolved gas as well as percolating gas. When the input rate is greater than the rate of removal, a positive pressure differential may be created such that the pressure in the interior atmosphere 3 rises above local atmospheric pressure. This may increase the rate at which percolating gas displaces previously dissolved gas from the liquid 2, again, facilitating the removal of previously dissolved gas.

Depending on the efficiency of the vacuum source, and the chemical properties of the liquid and gases employed, it may be necessary to repeat this process to remove the desired amount of previously dissolved gas from the liquid 2. To remove a greater amount of the dissolved gas, after each round, the tank 1 may be removed from the vacuum source 6 and gas line 80 with the respective sealing mechanisms 5 and 85 in the closed state, or only sealing mechanism 5 in the embodiment depicted in FIG. 8a. The tank 1 may then be set aside for a short period (e.g., usually less than about 1 hour, again depending upon the chemical properties of the liquid and gases employed) to stabilize and equilibrate. Upon stabilization, the gas removal source 6 and gas line 80 may be reconnected and another round may commence.

Once the desired amount of previously dissolved gas has been removed from the liquid 2, having been displaced by the percolating gas, the tank 1 may be suspended with the opening 4 facing downward. A filling supply line may be coupled to the opening 4 so that liquid 2 may be transferred via filling equipment (not shown) to any suitable container. In order to accomplish transfer of the liquid 2 through the filling supply line, any pressure difference which might exist (e.g., if the input rate of percolating gas was less than the removal rate by the vacuum source 6) between the interior atmosphere 3 and the opening 4 may be overcome by the force of gravity and/or suction force applied via the filling equipment and filling supply line, similar to that described in the first embodiment.

In a sixth embodiment of the instant invention, a liquid may be de-gassed by a process known to those skilled in the art as "salting out," which is based on the principle that more soluble reagents will exclude less soluble reagents from a solution. In this embodiment, the liquid is a concentrated solution of sodium chloride, phosphate-buffered saline, or any other appropriate salt or buffer solution. A pharmaceutical active, or the like, may be concentrated therein, as well, and may preferably be included in a concentration higher than that which is desirable at the time of injection. The concentrations of the salt or buffer and the pharmaceutical active may be as high as maximum saturation, respectively, for the liquid. When the respective concentrations are sufficiently high, which may be at a point significantly lower than maximum saturation depending on the solvents and solutes under consideration, substantially no gas may remain dissolved in the liquid. This liquid may be filled into a container via filling equipment. De-gassed water or another appropriate de-gassed solvent may be added to the liquid to dilute the liquid to an appropriate concentration. The addition of the de-gassed water or other appropriate de-gassed solvent may occur either prior to or following filling of a container with the "salted out" liquid. Alternatively, the de-gassed water or other appropriate de-gassed solvent may be added to the liquid immediately prior to administering a needle-less injection. This latter alternative may be particularly advantageous when the chemistry of a pharmaceutical active is such that it will break down soon after a solvent is added thereto, or in instances where heating or vacuum de-gassing is not a viable alternative.

Similar to "salting out," in a seventh embodiment of the instant invention, a liquid may be de-gassed by raising the concentration of solute therein to such a level that substantially no gas can remain dissolved. Such a de-gassed liquid may be filled into a container suitable for use with the instant invention. This liquid can be diluted with de-gassed water or another appropriate de-gassed solvent either prior to or following filling with the concentrated, de-gassed liquid. Alternatively, the de-gassed water or other appropriate de-gassed solvent may be added to the liquid immediately prior to administering a needle-less injection. As above, this latter alternative may be particularly advantageous when the chemistry of a pharmaceutical active is such that it will break down soon after a solvent is added thereto, or in instances where heating or vacuum de-gassing is not a viable alternative.

Figure 3:
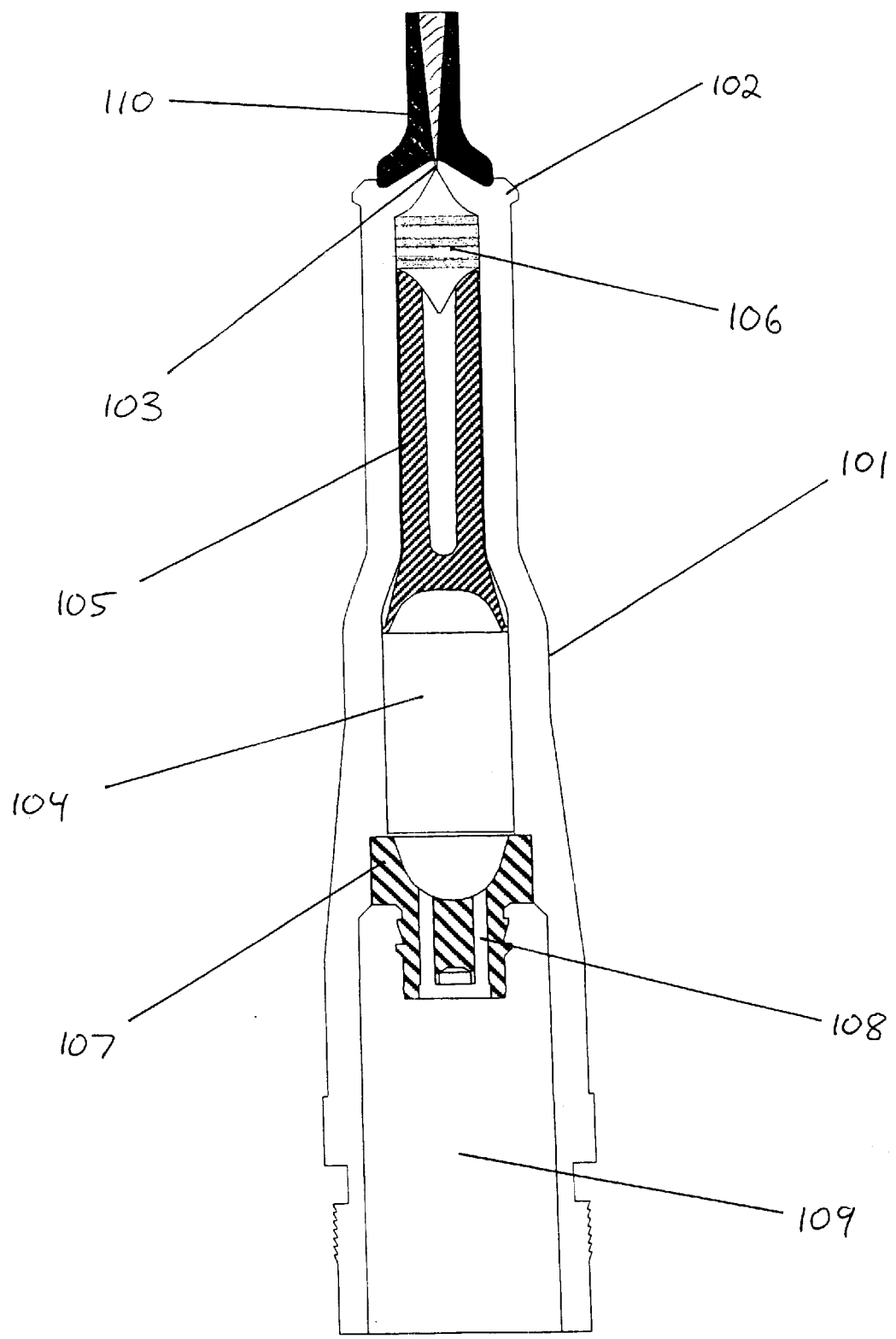
FIG. 3 illustrates a cross-section of an ampoule housing of a needle-less injector prior to filling.

As depicted in FIG. 3, an ampoule housing 101 is one container suitable for use in accordance with the instant invention. For purposes of the instant invention, the term "ampoule housing" refers to ampoule housings of needle-less injectors of any suitable variety, but further encompasses ampoules used in conjunction with needle-less injectors that do not comprise the entirety or a substantial majority of the housing requisite for a complete needle-less injector housing. Thus, as used herein, the term "ampoule housing" encompasses the term "ampoule," as it is normally construed, as well.

Furthermore, the ampoule housing 101 or other suitable container need not be of the shape illustratively depicted herein. The ampoule housing 101 may be employed as an integral part of the main housing of a needle-less injector which, in alternate embodiments, may contain finger rests, or the like. Moreover, ampoules may take a variety of forms, many of which are mechanically separable from the housing of a needle-less injector, yet the filling of these ampoules is both contemplated herein and is accomplished in a substantially similar manner to the filling of the ampoule housing 101 illustratively depicted herein.

An ampoule housing 101 may be possessed of a dispensing end 102 with a dispensing orifice 103. The ampoule housing 101 may be fitted with a piston 105 and plunger 106, both of which may be pressure fitted within the interior cavity 104 of ampoule housing 101. The plunger 106 may be symmetrical in shape along a plane perpendicular to its direction of travel within the interior cavity 104. Once the piston 105 and plunger 106 are inserted into the ampoule housing 101, the ampoule housing 101 may further be fitted with a diffuser 107. The diffuser 107 may be permanently affixed to the ampoule housing 101 by high frequency welding, or any other suitable means. Moreover, the interior cavity 104 is spatially defined by that portion of the interior wall of the ampoule housing 101 extending from the dispensing end 102 to the diffuser 107. Piston 105 and plunger 106 reside entirely within the interior cavity 104, and move solely within the interior cavity 104 in the embodiment depicted in FIG. 3, however, in alternative embodiments, the interior cavity may not be so defined. The interior cavity 104 is preferably of a roughly cylindrical shape, though it may take another geometric configuration in alternative embodiments. In preferred embodiments, the diffuser 107 is possessed of at least one channel 108 that allows air to flow between the interior cavity 104 and the engine chamber 109. During filling of the ampoule housing 101, an engine assembly (not shown) is preferably not present in the ampoule housing 101, thus the at least one channel 108 in the diffuser 107 provides air flow between the interior cavity 104 and the local atmosphere.

Once the piston 105 and plunger 106 are fitted into the ampoule housing 101, and the diffuser 107 affixed thereto, the assembly may be prepared for gamma sterilization, and so sterilized, commensurate with a medical, veterinary, or other similar function of the assembly. Sterilization by other means may be employed, in accordance with the intended use of the ampoule or other container employed with the methods of the instant invention. Moreover, the ampoule housing 101 or other suitable container may be alternatively or additionally sterilized at a different stage of preparation for use, or may not be sterilized at all.

To load the liquid 2 into the ampoule housing 101 or other container, the tank may be connected via filling equipment (not shown) that terminates in an input line 110 placed in contact with the dispensing end 102 of the ampoule housing 101, allowing for fluid communication therebetween. The input line 110 may be temporarily, mechanically affixed to the dispensing end 102 of the ampoule housing 101, or may solely be brought into contact with the dispensing end 102 of the ampoule housing 101, as depicted in FIG. 3. In preferred embodiments, the interior cavity 104 is substantially free of air in the region between the plunger 106 and dispensing end 102 of the ampoule housing 101 prior to filling the ampoule housing 101 with liquid 2. This may be accomplished by designing the contour of the portion of the plunger 106 that abuts the wall of the interior cavity 104 at the dispensing end 102 to sufficiently mirror the contour of the wall of the interior cavity 104 at the dispensing end 102. Alternatively, the material employed to construct the plunger 106 may be of sufficient elastic properties such that when the plunger 106 is in mechanical contact with the dispensing end 102, the plunger 106 substantially conforms in shape to the contour of the wall of the interior cavity 104 at dispensing end 102.

Figure 4:
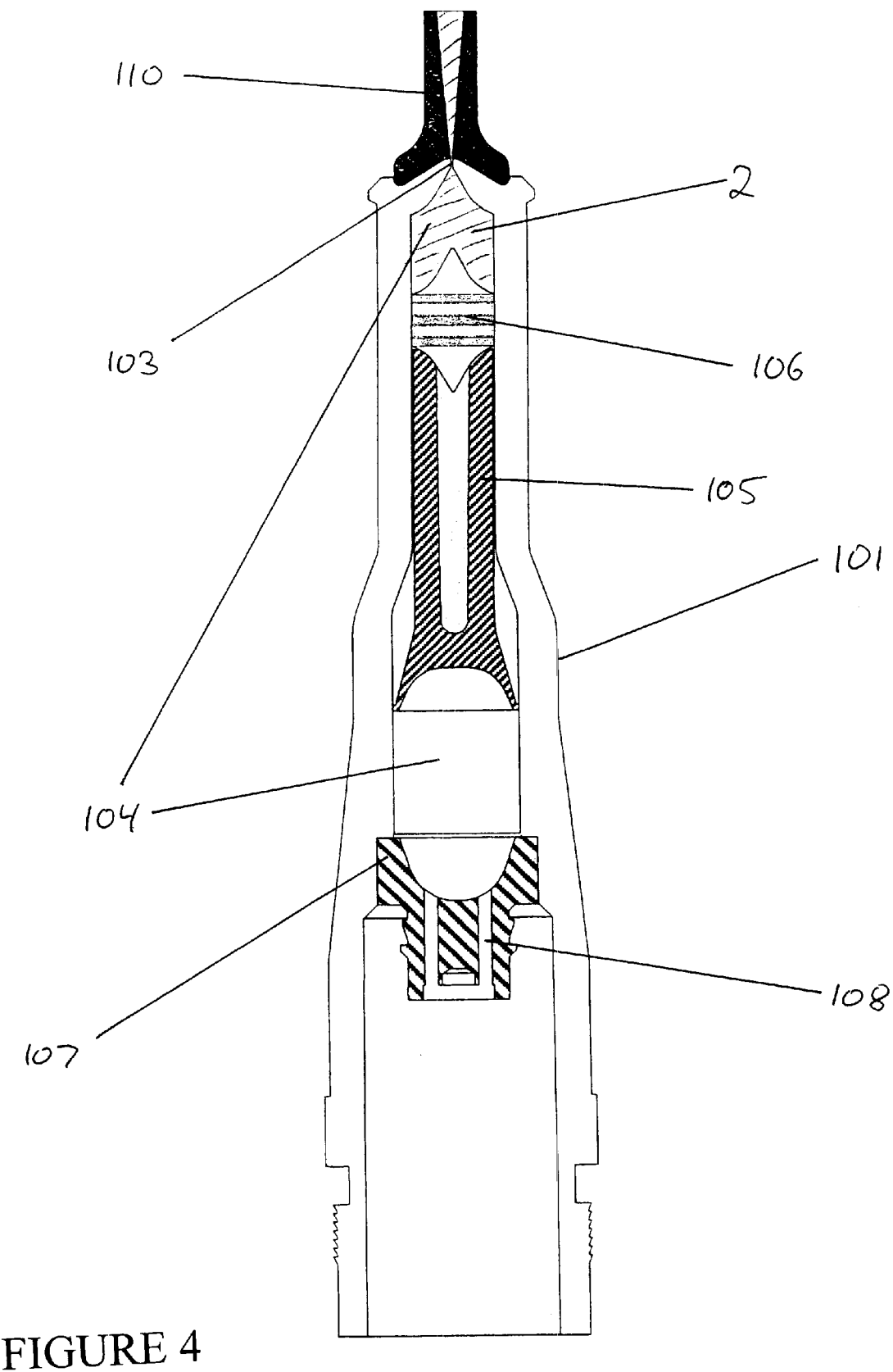
FIG. 4 illustrates a cross-section of an ampoule housing of a needle-less injector during filling.

As depicted in FIG. 4, filling of the interior cavity 104 of the ampoule housing 101 or other suitable container may be accomplished by pushing the liquid 2 from the tank, via the filling equipment and input line 110, through the dispensing orifice 103 of the ampoule housing 101 and into the portion of the interior cavity 104 proximate to the dispensing end 102 of the ampoule housing 101, or other suitable container. The force required to drive the liquid 2 from the tank may be derived from gravity by inverting the tank, by pressure feed, or by any other suitable means via the filling equipment.

As depicted in FIG. 4, as the interior cavity 104 is filled with liquid 2, plunger 106 and piston 105 may be forced through interior cavity 104, toward the diffuser 107. The air initially present in the portion of the interior cavity 104 between the surface of the piston 105 distal to the dispensing end 102 and the diffuser 107 may be simultaneously forced out of the interior cavity 104 through the at least one channel 108 in the diffuser 107.

Figure 5A:
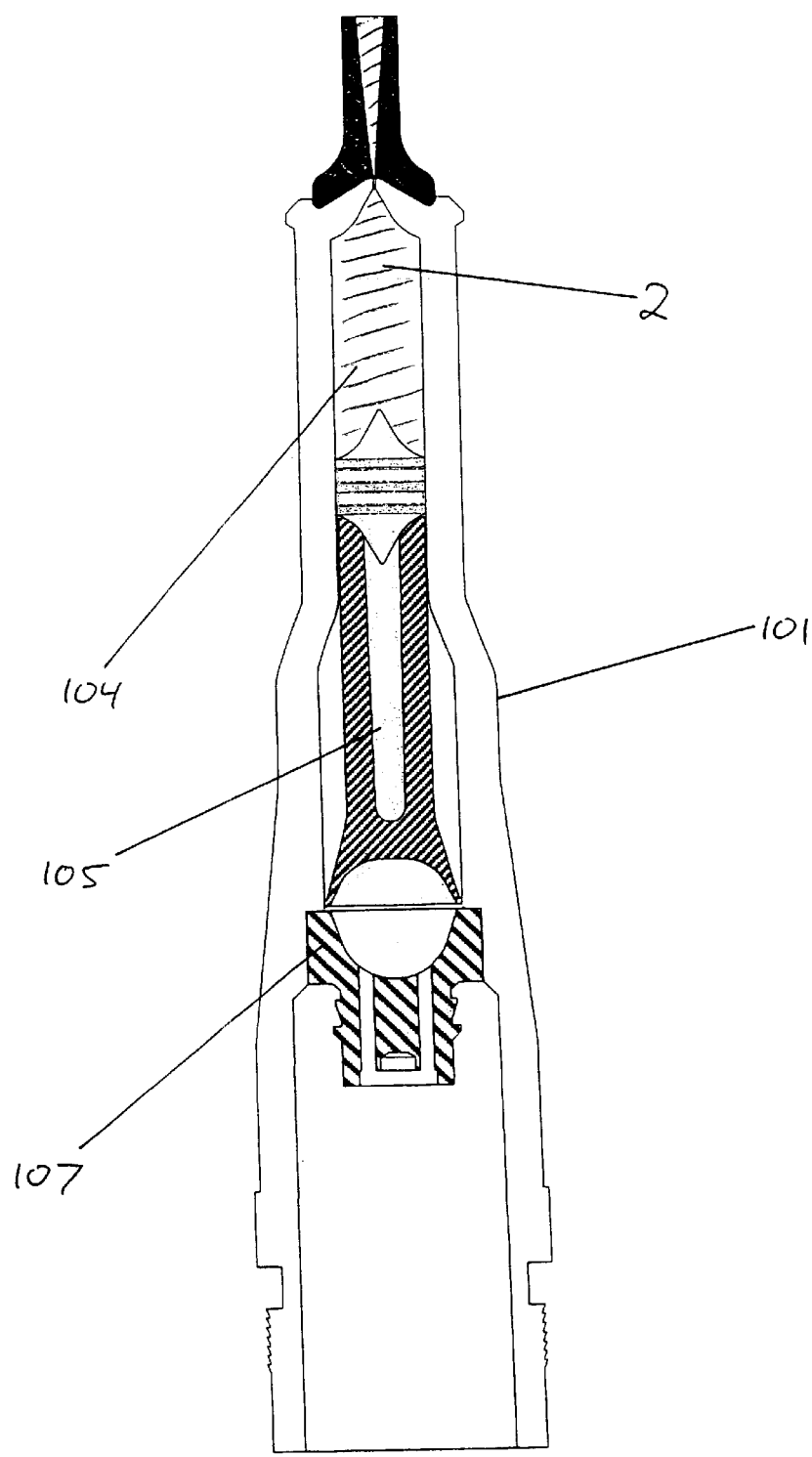
FIG. 5a illustrates a cross-section of an ampoule housing of a needle-less injector once filling is complete.

In one embodiment of the instant invention, liquid 2 is forced into the interior cavity 104 of the ampoule housing 101 until the piston 105 comes to rest against the diffuser 107, as depicted in FIG. 5a, wherein the ampoule housing may preferably be filled with from approximately $\frac{1}{20}$ cc to 1 cc of liquid 2. However, in alternate embodiments filling may be ceased prior to the piston 105 and diffuser 107 coming into mechanical contact. In these latter embodiments, an ampoule or other container may be filled with multiple liquids, which may be accomplished by first partially filling the interior cavity 104 with a first liquid, and then partially filling the interior cavity 104 with a second liquid, and so on. For example, a "salted out" solution in accordance with an embodiment of the instant invention may partially fill the interior cavity 104 of the ampoule housing 101. Following partial filling with such a solution, the remainder of the interior cavity 104 may be filled with de-gassed water. In yet further embodiments, the interior cavity 104 may be partially filled with a liquid, and another liquid may be added to complete the filling process at a later time, often just prior to injection.

Figure 5B:
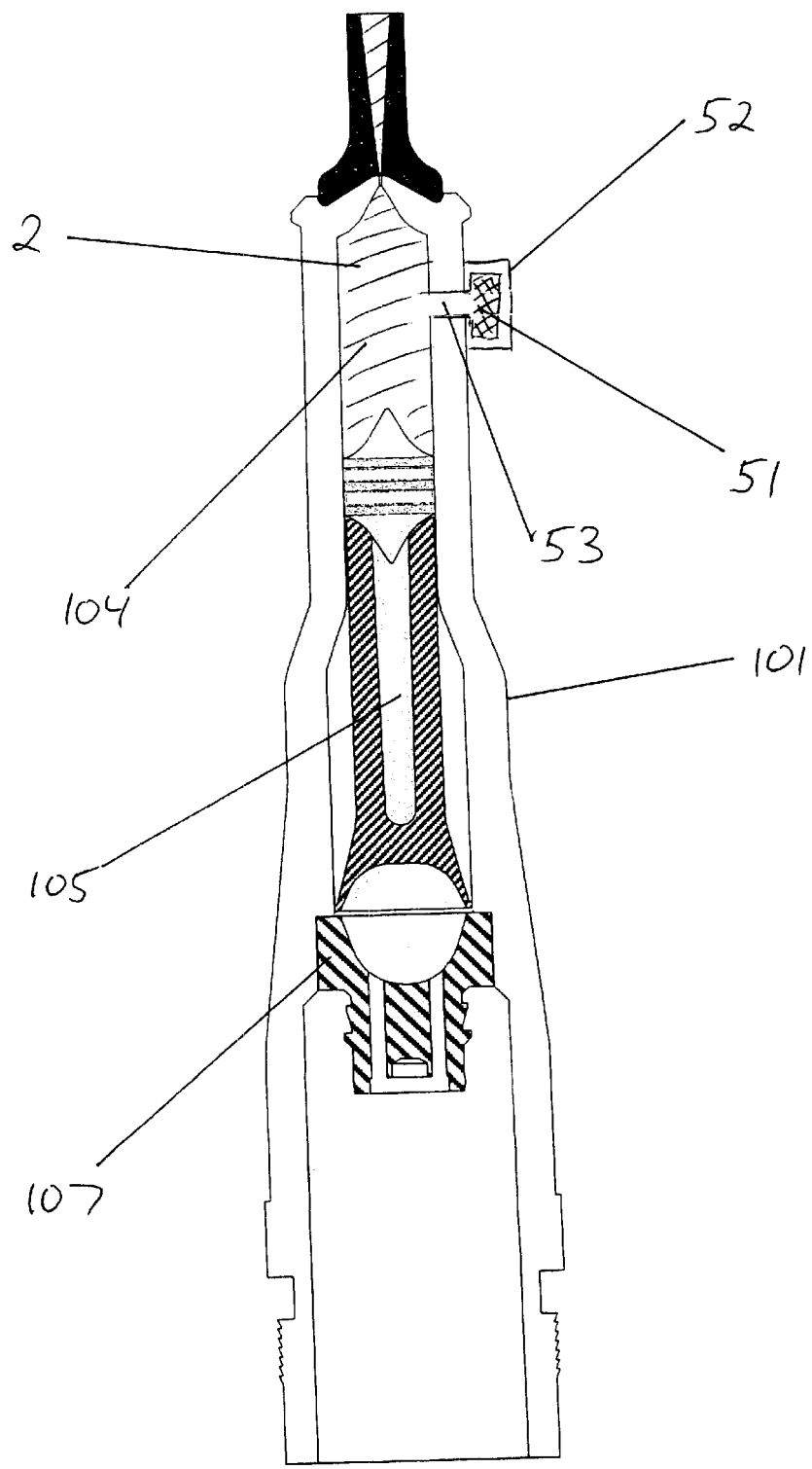
FIG. 5b illustrates the cross-section of a similar ampoule housing, this housing additionally fitted with an exterior compartment.

As depicted in FIG. 5b, the ampoule housing 101 may be fitted with an exterior compartment 52 that contains an absorbent material 51. A small diameter hole 53 allows for gaseous, but not fluid communication between the absorbent material 51 contained within exterior compartment 52, and the interior cavity 104 of the ampoule housing 101. The hole 53 may be formed by laser, or other device capable of creating a small, precise hole. Where a liquid 2 contains a gas that may be absorbed by absorbent material 51, that gas may be extracted from the liquid 2 after filling by absorption, thereby de-gassing the liquid 2.

Figure 6:
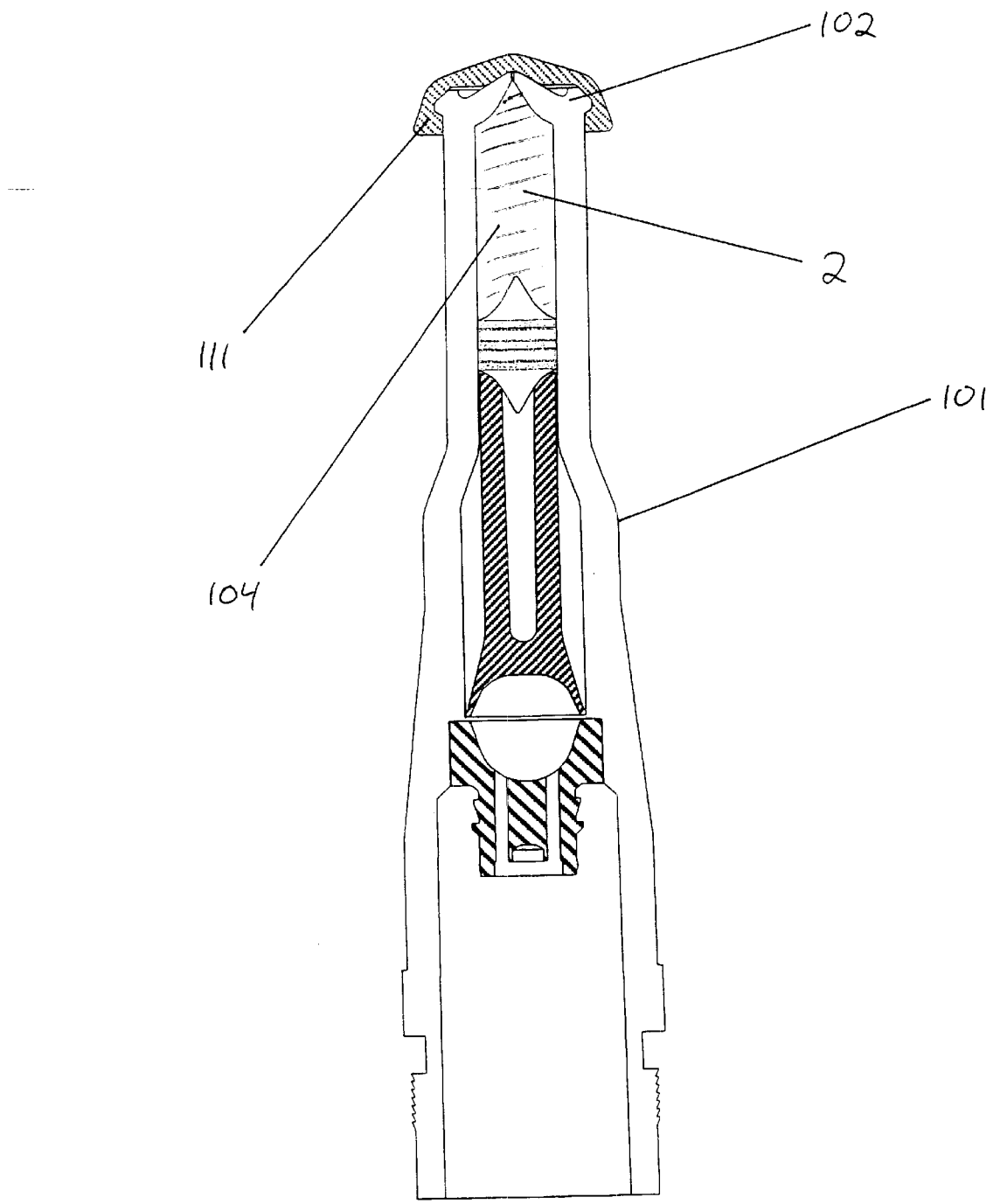
FIG. 6 illustrates a cross-section of a capped ampoule housing of a needle-less injector after filling with de-gassed liquid.

As depicted in FIG. 6, once filling is completed, the input line 110 is removed from the ampoule housing 101, and the dispensing end 102 of the ampoule housing 101 may be fitted with a self-sealing cap 111. The ampoule may now be stored for substantial periods of time and at a variety of temperature conditions with a minimized chance of developing a gas pocket within the interior cavity 104, now filled with liquid 2.

Figure 7:
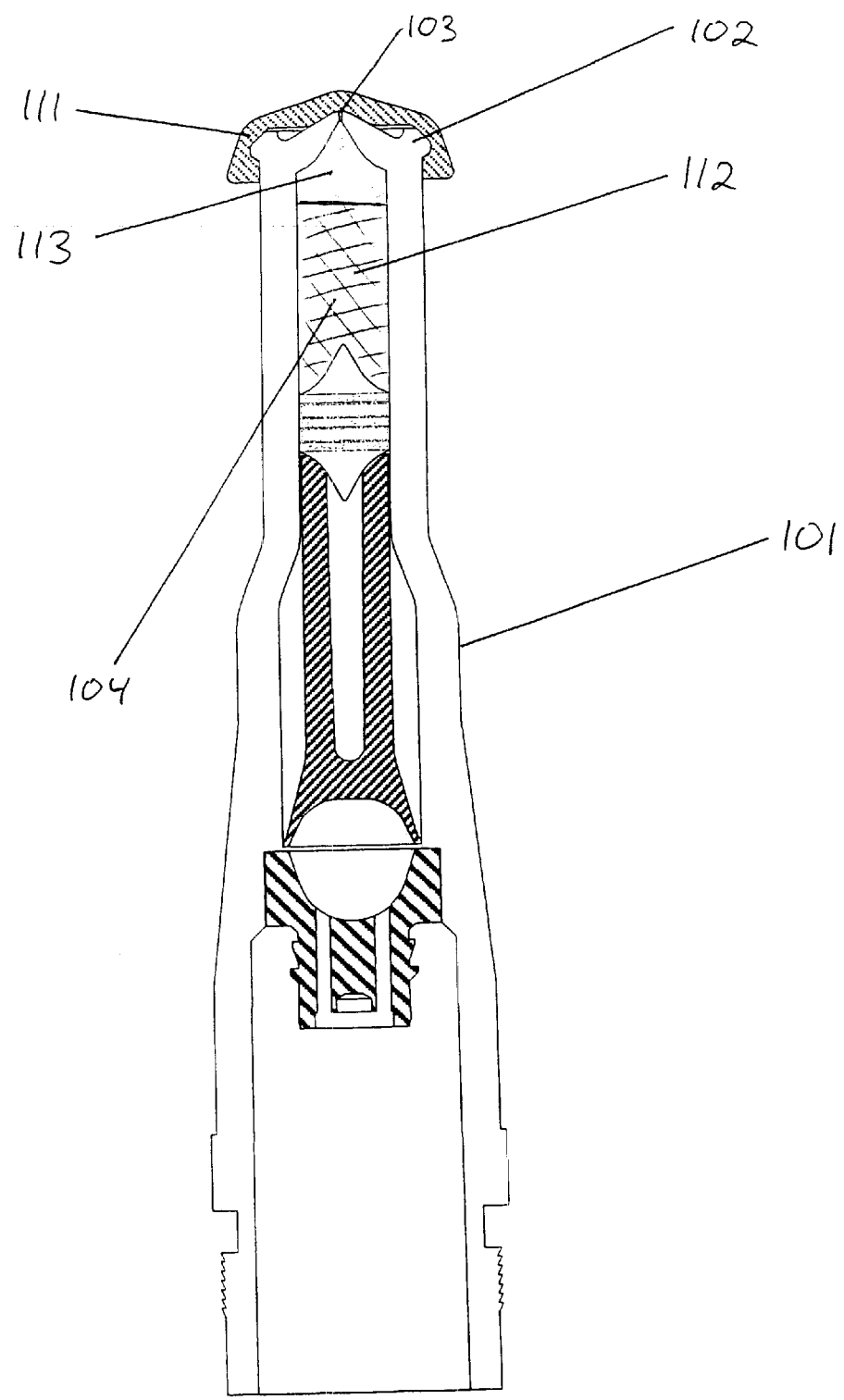
FIG. 7 illustrates a cross-section of a capped ampoule housing of a needle-less injector after filling with liquid that has developed an air pocket.

As depicted in FIG. 7, an ampoule housing 101 or other container filled with liquid that has not been de-gassed 112 may develop a gas pocket 113, which often collects at the dispensing end 102 of the interior cavity 104. Orientation of the ampoule housing 101 in storage may cause a gas pocket to collect in a portion of the interior cavity 104 other than near the dispensing end 102, yet removal of the self-sealing cap 111 prior to use may cause the gas pocket to migrate toward the dispensing orifice 103. This migration may further cause a small amount of the liquid to escape through the dispensing orifice 103 prior to injection, thereby reducing the amount of liquid available for injection. Moreover, when the ampoule housing 101 is employed in conjunction with a needle-less injector and the liquid deployed therefrom, the gas pocket 113 may contact the skin of a patient prior to the liquid, oftentimes resulting in a subdermal hematoma. The ampoule housing 101 in FIG. 6 has been filled with de-gassed liquid 2 (whether that liquid was de-gassed prior to filling, or whether it de-gassed itself by nature of a percolating gas having been dissolved therein), and thus develops substantially no such gas pocket.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method for removing a gas from a liquid containing said gas, the method comprising:

partially filling a tank with said liquid containing said gas, said tank having an interior atmosphere;

reducing the pressure of said interior atmosphere; and removing said gas as it escapes from said liquid into said interior atmosphere, wherein the liquid is an injectable medication.

2. The method according to claim 1, further including rolling said tank while the pressure of said interior atmosphere is reduced.

3. The method according to claim 1, wherein said interior atmosphere is in contact with said liquid along an interface having a surface area, and said method further including tilting said tank to maximize said surface area of said interface.

4. The method according to claim 1, wherein said tank has an opening and wherein said opening is coupled to a sealing mechanism, and reducing said pressure includes:

coupling a gas removal source to one of said sealing mechanism and said opening;

placing said sealing mechanism in the opened state; and applying vacuum pressure to said interior atmosphere through said gas removal source.

5. The method according to claim 1, wherein the steps of reducing the pressure of said interior atmosphere and of removing said gas are repeated after allowing said liquid to stabilize.

6. The method according to claim 1, further including heating said tank while said pressure of said interior atmosphere is reduced.

7. The method according to claim 1, further including sending sound waves through said liquid, wherein said sound waves originate from a device immersed in said liquid.

8. The method according to claim 1, wherein said liquid contains water and a portion of said water is removed from said liquid in the form of water vapor during said removal of said gas, and said method further including adding de-gassed water to said liquid to compensate for said removal of said water vapor.

9. The method according to claim 1, further including sterilizing said tank.

10. A method for filling a container with a de-gassed liquid, said liquid containing a gas prior to being filled into said container, said method comprising:

partially filling a tank with said liquid containing said gas, said tank having an interior atmosphere and an opening;

reducing the pressure of said interior atmosphere;

removing said gas as it escapes from said liquid into said interior atmosphere; filling said container with said liquid after said gas has been removed from said liquid; and sealing said container, wherein said liquid is an injectable medication.

11. The method according to claim 10, further including rolling said tank as said pressure of said interior atmosphere is being reduced.

12. The method according to claim 10, wherein filling said container includes tilting said tank so that said liquid is transferred from said tank through said opening by means of gravity.

13. The method according to claim 10, wherein said opening is coupled to a sealing mechanism, and reducing said pressure includes:

coupling a gas removal source to one of said sealing mechanism and said opening;

placing said sealing mechanism in the opened state; and applying vacuum pressure to said interior atmosphere through said gas removal source.

14. The method according to claim 10, further including heating said tank while said pressure of said interior atmosphere is reduced.

15. The method according to claim 10, further including sending sound waves through said liquid, wherein said sound waves originate from a device immersed in said liquid.

16. The method according to claim 10, wherein said liquid contains water and further wherein a portion of said water is removed from said liquid in the form of water vapor during said removal of said gas, said method further including adding de-gassed water to said liquid to compensate for said removal of water vapor.

17. The method according to claim 10, further including sterilizing said tank.

18. The method according to claim 10, wherein said container is an ampoule.

19. The method according to claim 18, further including fitting said ampoule with a plunger, a piston and a diffuser prior to filling said ampoule with said liquid.

20. The method according to claim 19, wherein said ampoule has a dispensing end, and wherein prior to filling said ampoule with said liquid, said plunger is in contact with said dispensing end of said ampoule.

21. The method according to claim 19, wherein after filling said ampoule with said liquid, said piston is in contact with said diffuser.

22. The method according to claim 18, wherein said ampoule is sealed with a self-sealing cap after filling said ampoule with said liquid.

23. The method according to claim 18, wherein said ampoule is filled with from about $1/20$ cc to about 1 cc of said de-gassed liquid.

24. A system for removing a gas from a liquid containing said gas, said system comprising:
- a tank partially filled with said liquid, said liquid having said gas dissolved therein, said tank having an opening;
- a sealing mechanism coupled to said opening; and
- a vacuum pressure source configured to be coupled to one of said sealing mechanism and said opening, wherein said liquid is an injectable medication and said sealing mechanism is in the opened state when said vacuum pressure source is coupled to the one of said sealing mechanism and said opening.

25. The system according to claim 24, said system further including a roller in contact with an exterior surface of said tank such that said tank rolls as said roller rotates.

26. The system according to claim 24, said system further including a heating element in contact with an exterior surface of said tank such that said liquid partially filling said tank is heated.

27. The system according to claim 24, said system further including a sound wave generating rod immersed in said liquid such that sound waves are propagated through said liquid.

28. The system according to claim 24, said system further including a filling supply line configured to be coupled to at least one of said opening and said sealing mechanism and adapted to transfer said liquid to a container capable of being sealed.

29. The system according to claim 24, wherein said container is an ampoule.

30. A method for filling a container with a liquid that de-gasses after filling, said liquid containing a gas prior to being filled into said container, said method comprising:
- partially filling a tank with said liquid containing said gas, said tank having an interior atmosphere and an opening;
- percolating a percolating gas through said liquid;
- removing both said gas and a portion of said percolating gas as said gas and said portion of said percolating gas escape from said liquid into said interior atmosphere;
- filling said container with said liquid after said gas has been removed from said liquid; and
- sealing said container.

31. The method according to claim 30, wherein a volume of said percolating gas remains dissolved in said liquid upon filling said liquid into said container, and wherein said percolating gas separates from said liquid after said liquid is filled into said container.

32. The method according to claim 30, wherein said opening is coupled to a sealing mechanism, and removing both said gas and said portion of said percolating gas includes:
- coupling a gas removal source to one of said sealing mechanism and said opening;
- placing said sealing mechanism in the opened state; and
- applying vacuum pressure to said interior atmosphere through said gas removal source.

33. The method according to claim 30, wherein said percolating gas is an inert gas.

34. The method according to claim 30, wherein said percolating gas is helium.

35. The method according to claim 30, wherein said container is gas permeable to said percolating gas, and wherein said percolating gas diffuses out of said container.

36. The method according to claim 30, wherein said container is at least partially comprised of an extracting material, and wherein said method further comprises said percolating gas chemically reacting with said extracting material.

37. The method according to claim 30, wherein said container is an ampoule,
- wherein said ampoule is fitted with a mechanical element,
- wherein said mechanical element is at least partially comprised of an extracting material, and
- wherein said separation of said percolating gas from said liquid comprises said percolating gas chemically reacting with said extracting material.

38. The method according to claim 30, wherein said container is an ampoule,
- wherein said ampoule possesses an interior cavity,
- wherein said interior cavity is coated with an extracting material, and
- wherein said method further comprises said percolating gas chemically reacting with said extracting material.

39. The method according to claim 30, wherein said container is an ampoule,
- wherein said ampoule possesses an interior cavity and an exterior compartment,
- wherein said interior cavity and said exterior compartment are in gaseous communication,
- wherein said exterior compartment contains an absorbent material, and
- wherein said method further comprises said percolating gas chemically reacting with said absorbent material.

40. The method according to claim 30, wherein said removal of both said gas and said portion of said percolating gas is performed at a rate relative to a percolation rate of said percolating gas that is selected from the group consisting of greater than, equal to, and less than said percolation rate.

41. The method according to claim 30, wherein a remainder of said percolating gas resides in said tank after said percolation is complete, said method further including removing said remainder of said percolating gas from said tank.

42. A method of filling an ampoule comprising:
- providing a de-gassed liquid, and
- filling said ampoule with said de-gassed liquid.

43. The method according to claim 42, wherein said de-gassed liquid is an injectable medication.

44. The method according to claim 42, wherein said ampoule remains substantially free of gas pockets after said filling.

45. The method according to claim 42, wherein said de-gassed liquid is selected from the group consisting of a highly concentrated solution, a solution in combination with a highly concentrated salt solution, and a solution in combination with a highly concentrated buffer solution,
- wherein said de-gassed liquid is of a sufficiently high concentration such that it is substantially gas free.

46. The method according to claim 42, wherein providing said de-gassed liquid comprises:
- partially filling a vessel with a solute,
- removing the gas from said vessel, and
- adding a de-gassed solvent to said vessel, wherein said solvent and said solute are mixed in said vessel,
- wherein said vessel remains substantially gas-free.

47. A method of filling an ampoule comprising:
- providing a de-gassed liquid,
- partially filling said ampoule with said de-gassed liquid,
- providing a de-gassed solvent, and partially filling said ampoule with said de-gassed solvent, wherein said de-gassed liquid is selected from the group consisting of a highly concentrated solution, a solution in combination with a highly concentrated salt solution, and a solution in combination with a highly concentrated buffer solution, wherein said de-gassed liquid is of a sufficiently high concentration such that it is substantially gas free.

48. A method of filling an ampoule comprising:

providing a liquid with a gas dissolved therein, and filling said ampoule with said liquid, wherein said gas separates from said liquid, and wherein after said separation said liquid remains substantially free of said gas.

49. The method according to claim 48, wherein said ampoule is gas permeable to said gas, and wherein said separation comprises said gas diffusing out of said ampoule.

50. The method according to claim 48, wherein said ampoule is at least partially comprised of an extracting material, and wherein said separation comprises said gas chemically reacting with said extracting material.

51. The method according to claim 48, wherein said ampoule is fitted with a mechanical element, wherein said mechanical element is at least partially comprised of an extracting material, and wherein said separation comprises said gas chemically reacting with said extracting material.

52. The method according to claim 48, wherein said ampoule possesses an interior cavity, wherein said interior cavity is coated with an extracting material, and wherein said separation comprises said gas chemically reacting with said extracting material.

53. The method according to claim 48, wherein said ampoule possesses an interior cavity and an exterior compartment, wherein said interior cavity and said exterior compartment are in gaseous communication, wherein said exterior compartment contains an absorbent material, and wherein said separation comprises said gas chemically reacting with said absorbent material.

54. The method according to claim 48, wherein said liquid is an injectable medication.

55. A method for administering an injection with a needle-less injector, wherein said needle-less injector is fitted with an ampoule, said method comprising:

filling said ampoule with a de-gassed liquid, assembling said ampoule in said needle-less injector, and administering said injection.

* * * * *